(12) United States Patent
Dayel et al.

(10) Patent No.: US 11,119,110 B2
(45) Date of Patent: Sep. 14, 2021

(54) LOW-VOLUME COAGULATION ASSAY

(71) Applicant: Theranos, Inc., Palo Alto, CA (US)

(72) Inventors: Mark Dayel, Palo Alto, CA (US); Samartha Anekal, Palo Alto, CA (US); Paul Patel, Palo Alto, CA (US); Ian Gibbons; Elizabeth A. Holmes, Palo Alto, CA (US)

(73) Assignee: Labrador Diagnotics LLC, Wilmington, DE (US)

( * ) Notice: Subject to any disclaimer, the term of this patent is extended or adjusted under 35 U.S.C. 154(b) by 0 days.

(21) Appl. No.: 14/598,817

(22) Filed: Jan. 16, 2015

(65) Prior Publication Data

US 2015/0301018 A1 Oct. 22, 2015

Related U.S. Application Data

(63) Continuation of application No. PCT/US2013/051162, filed on Jul. 18, 2013.

(60) Provisional application No. 61/673,227, filed on Jul. 18, 2012.

(51) Int. Cl.
*G01N 33/86* (2006.01)
*G01N 33/58* (2006.01)
*G01N 33/49* (2006.01)
*G01N 21/84* (2006.01)
*C12Q 1/56* (2006.01)

(52) U.S. Cl.
CPC ............ *G01N 33/86* (2013.01); *C12Q 1/56* (2013.01); *G01N 21/84* (2013.01); *G01N 33/4905* (2013.01); *G01N 33/582* (2013.01); *G01N 2333/75* (2013.01)

(58) Field of Classification Search
None
See application file for complete search history.

(56) References Cited

U.S. PATENT DOCUMENTS

| | | | |
|---|---|---|---|
| 5,840,573 A | * | 11/1998 | Fields ............... B01L 3/502 435/287.2 |
| 6,582,964 B1 | | 6/2003 | Samsoondar et al. |
| 6,838,055 B2 | | 1/2005 | Sando et al. |
| 7,130,046 B2 | | 10/2006 | Fritz et al. |
| 7,291,497 B2 | | 11/2007 | Holmes et al. |
| 7,807,351 B2 | | 10/2010 | Sode et al. |

(Continued)

FOREIGN PATENT DOCUMENTS

| | | |
|---|---|---|
| JP | 2002055109 A | 2/2002 |
| WO | 2002022852 A2 | 3/2002 |

OTHER PUBLICATIONS

Cannon PowerShot S3 IS: Digital Photography Review, Feb 2006.
(Continued)

*Primary Examiner* — Jill A Warden
*Assistant Examiner* — Brittany I Fisher

(57) ABSTRACT

Compositions and methods for measuring coagulation parameters using very small volumes of blood are provided. Advantageously, the methods described herein can be performed from a single drop of blood (about 20 µL) while generally leaving enough sample to perform other measurements, optionally in a multiplexed format. The methods and devices do not require a skilled operator and can be performed at the point of service, which can be an important feature for managing blood coagulation disorders and treatments thereof.

20 Claims, 19 Drawing Sheets

(56) References Cited

U.S. PATENT DOCUMENTS

| | | |
|---|---|---|
| 7,888,125 B2 | 2/2011 | Gibbons et al. |
| 8,012,744 B2 | 9/2011 | Gibbons et al. |
| 8,088,593 B2 | 1/2012 | Burd et al. |
| 8,194,235 B2 | 6/2012 | Kosaka et al. |
| 8,435,738 B2 | 5/2013 | Holmes |
| 2002/0064483 A1 | 5/2002 | Sando et al. |
| 2004/0237970 A1 | 12/2004 | Vournakis et al. |
| 2005/0233466 A1 | 10/2005 | Wright et al. |
| 2006/0141629 A1* | 6/2006 | Gitel ............... G01N 33/4905 436/69 |
| 2006/0264783 A1 | 11/2006 | Holmes et al. |
| 2007/0031515 A1 | 2/2007 | Stucky et al. |
| 2007/0073590 A1* | 3/2007 | Cosentino ............ A61B 5/6887 705/22 |
| 2007/0170054 A2 | 7/2007 | Wilsey |
| 2007/0224084 A1 | 9/2007 | Holmes et al. |
| 2008/0038764 A1 | 2/2008 | Yin |
| 2008/0096285 A1* | 4/2008 | Koyata ................ G01N 21/59 436/164 |
| 2009/0061468 A1 | 3/2009 | Hoshiko et al. |
| 2009/0148882 A1* | 6/2009 | Goldstein ............... B01L 3/508 435/29 |
| 2009/0202621 A1* | 8/2009 | Maldonado ............ A61K 9/127 424/450 |
| 2009/0318775 A1 | 12/2009 | Michelson et al. |
| 2010/0059414 A1 | 3/2010 | Sturm et al. |
| 2010/0081144 A1 | 4/2010 | Holmes et al. |
| 2010/0086953 A1 | 4/2010 | Kappel et al. |
| 2010/0248278 A1 | 9/2010 | Pouteau et al. |
| 2011/0045577 A1 | 2/2011 | Bruzewicz et al. |
| 2011/0093249 A1 | 4/2011 | Holmes et al. |
| 2011/0104725 A1 | 5/2011 | Pamula et al. |
| 2011/0312002 A1 | 12/2011 | Taktak et al. |
| 2012/0309636 A1 | 12/2012 | Gibbons et al. |
| 2014/0087403 A1 | 3/2014 | Dayel et al. |

OTHER PUBLICATIONS

Faivre, M. et al., Coagulation dynamics of a blood sample by multiple scattering analysis. J. Biomed. Opt., May 4, 2011, vol. 16, No. 5, pp. 057001-1-057001-9.

Faxalv et al. Imaging of blood plasma coagulation and its propagation at surfaces. J Biomed Mater Res A, Jun. 2008, 85 (4): 1129-34.

Office Action dated Dec. 30, 2015 for U.S. Appl. No. 13/944,863.

Notice of Allowance dated May 6, 2016 for U.S. Appl. No. 13/944,863.

Piederriere et al. Evaluation of blood plasma coagulation dynamics by speckle analysis. J. Biomed. Opt., Mar. 22, 2004, vol. 9, No. 2, pp. 408-412.

Office Action dated Jul. 24, 2015 for U.S. Appl. No. 13/944,863.

Nuttall, AL Techniques for the observation and measurement of red blood cell velocity in vessels of the guinea pig cochlea. Hearing Research 1987; vol. 27, p. 111, abstract.

The International Search Report and the Written Opinion for dated Mar. 7, 2014 Application No. PCT/US13/51162.

Office Action dated Mar. 24, 2017 for U.S. Appl. No. 15/166,699.

* cited by examiner

LOW-VOLUME COAGULATION ASSAY

CROSS REFERENCE

This application claims the benefit of U.S. Provisional Application No. 61/673,227 filed Jul. 18, 2012, which application is incorporated herein by reference in its entirety.

BACKGROUND

Coagulation is a complex process by which blood or blood plasma forms clots. It is an important part of homeostasis, the cessation of blood loss from a damaged vessel, wherein a damaged blood vessel wall is covered by a platelet and fibrin-containing clot to stop bleeding and begin repair of the damaged vessel. Since inadequate coagulation can lead to an increased risk of bleeding (hemorrhage) and excessive coagulation can lead to obstructive clotting (thrombosis), the coagulation process is tightly controlled and highly conserved throughout biology.

Blood coagulation disorders are very dangerous, and the therapeutic means to treat them and to control coagulation are difficult to manage and also dangerous. In addition, many patients are chronically treated with anticoagulant drugs such as warfarin after receiving replacement heart valves and need to be monitored. It is increasingly advantageous to be able to monitor coagulation parameters, in particular prothrombin time ("PT"; also expressed as the mathematical transform, International Normalized Ratio "INR") and Activated Partial Thromboplastin Time ("aPTT") as part of a more comprehensive health and therapy monitoring program in which biomarkers and other therapeutic agents are measured. PT, INR and aPTT can be measured in clinical laboratories using conventional methods requiring relatively large volumes of blood or plasma, typically 5 mL collected into fixed volume vacuum tubes. In order to improve monitoring of patient blood coagulation parameters, improvements in performing coagulation assays and measuring coagulation parameters are needed.

SUMMARY

The inventors have recognized a need for and provided a solution to the challenge of measuring coagulation parameters using very small volumes of blood samples. Advantageously, the methods described herein can be performed with a small quantity of blood or plasma derived from a single drop of blood (about 20 µL) while generally leaving enough sample to perform other measurements, optionally in a multiplexed format. The methods and devices do not require a skilled operator and can be performed at the point of service, which can be an important feature for managing blood coagulation disorders and treatments thereof by providing information useful in adjusting dosage and frequency of medication.

In some embodiments, methods for assaying coagulation include: A) monitoring coagulation in a very small volume of blood sample (e.g. 20 µl or less), and/or B) diluting all or part of a blood sample and using the diluted blood sample for an assay, thus reducing the total amount of sample used for the assay.

In one aspect, various techniques are provided for performing coagulation assays with diluted or undiluted samples. In one embodiment, a coagulation assay is performed in a small container which has a high surface to volume ratio which aids in the adhesion of an incipient clot to the surface of the container. In another embodiment, an exogenous material (for example, fibrinogen) which increases clot strength and/or the turbidity (due to light scattering) generated during the clotting process is added to a sample. In another embodiment, small beads are added to a blood sample, and video imaging is used to track the movement of the beads as they settle by gravity and then reduce or cease movement upon clot formation. In another embodiment, small fluorescent beads are added to a blood sample, and fluorescence microscopy is used to track the movement of beads as they are moved by Brownian motion, convention and/or airflow and reduce or cease movement upon clot formation. In another embodiment, a blood sample is propelled through a container by a force, and video imaging is used to track the movement of the sample and the reduction or cessation in movement of the sample in the container upon clot formation.

In one aspect, provided herein is a method for measuring coagulation time of a blood sample of a subject. The method comprises (a) initiating a coagulation reaction of the blood sample of the subject, (b) obtaining a set of images of the coagulation reaction, and (c) analyzing the set of images to measure the coagulation time of the blood sample.

In one aspect, provided herein is a method for measuring coagulation time of a blood sample of a subject. The method comprises (a) obtaining a blood sample from the subject from blood obtained from the subject via a non-venous route, (b) initiating a coagulation reaction of the blood sample, (c) obtaining a set of images of the coagulation reaction, and (d) analyzing the set of images to measure the coagulation time of the blood sample wherein the amount of time for carrying out steps (a) to (d) is less than or about 1 hour. In some embodiments, the amount of time for carrying out steps (a) to (d) is less than or about 30 minutes. In some embodiments, the amount of time for carrying out steps (a) to (d) is less than or about 10 minutes.

In some embodiments, 20, 19, 18, 17, 16, 15, 14, 13, 12, 11, 10, 9, 8, 7, 6, 5, 4, 3, 2, or 1 µl or less of blood sample is used for the coagulation assay.

In some embodiments, the volume of the coagulation reaction is less than or about 20, 19, 18, 17, 16, 15, 14, 13, 12, 11, 10, 9, 8, 7, 6, 5, 4, 3, 2, or 1 µl.

In some embodiments, an individual image of the set of images is pixilated and comprises at least 1, 10, 100, 500, 1000, 2000, 3000, 4000, 5000, 6000, 7000, 8000, 9000, or 10,000 pixels.

In some embodiments, the method further comprises diluting the blood sample such that the coagulation time of the sample after dilution is between about 30 seconds and about 10 minutes.

In some embodiments, the method further comprises adding fibrinogen to the coagulation reaction.

In some embodiments, the initiating step comprises adding a coagulation initiation reagent to the blood sample.

In some embodiments, the blood sample is a plasma sample.

In some embodiments, the blood sample is obtained using a finger prick.

In some embodiments, the images are light scattering images of the coagulation reaction.

In some embodiments, the coagulation time is measured based on a transition of the intensity of the scattered light.

In some embodiments, the method further comprises adding a plurality of beads to the blood sample prior to obtaining the set of images. For example, at least 2, 3, 4, 5, 10, 100, or 1000 beads may be added to the blood sample.

In some embodiments, the plurality of beads include beads of at least two different sizes.

In some embodiments, the plurality of beads have sizes from about 1 µm to 5 µm.

In some embodiments, the plurality of beads have sizes from about 5 µm to 50 µm.

In some embodiments, the plurality of beads include one or more of polystyrene, latex, acrylic, or glass. In certain aspects, the beads may have a different refractive index from the reaction medium (e.g. higher or lower by about 1, 2, 3, 4, 5, 8, 10, 15, 16, 20, 25, 30, 35, 40, or 50%), or may be opaque. In addition, the beads may have a density different from the reaction medium (e.g. higher or lower by about 1, 2, 3, 4, 5, 8, 10, 15, 16, 20, 25, 30, 35, 40, or 50%). In some assays, the reaction medium has a density of about 1.01 g/cc.

In some embodiments, the step of analyzing the set of images comprises locating a time point when the beads become substantially motionless.

In some embodiments, the step of analyzing the set of images comprises locating the time point when a transition of the mobility of the beads occurs.

In some embodiments, the transition of the mobility of the beads is evidenced by deceleration of the settling of the beads in the coagulation reaction.

In some embodiments, the step of analyzing the set of images comprises comparing two images of the set of images to measure the motion of the beads.

In some embodiments, the beads are substantially motionless if the two images are substantially the same.

In some embodiments, the beads are labeled.

In some embodiments, the beads are labeled with a fluorescent label.

In another aspect, a method is provided for measuring a plurality of coagulation parameters of a blood sample of a subject. The method comprises (a) obtaining the blood sample of the subject, wherein the blood sample is less than or about 50 µl, (b) preparing a plasma sample from the blood sample, and (c) performing a plurality of assays using the plasma sample to measure the plurality of coagulation parameters, wherein at least one of the plurality of parameters is coagulation time.

In some embodiments, one of the coagulation parameters is selected from the group consisting of: Activated Partial Thromboplastin Time (aPTT), prothrombin time (PT), International Normalized Ratio (INR), bleeding time, coagulation factor, anti-phospholipid antibody, dilute Russell's viper venom time (dRVVT), and platelet function, thromboelastography (TEG or Sonoclot), and euglobulin lysis time (ELT).

In some embodiments, less than about 10 µl of the plasma sample is utilized for an individual assay of the plurality of assays. In some embodiments, less than about 2 µl of the plasma sample is utilized for an individual assay of the plurality of assays.

In some embodiments, the reaction volume of some or each of the plurality of assays is about or less than 6 µl. In some embodiments, the reaction volume of some or each of the plurality of assays is about or less than 10 µl.

In some embodiments, the amount of time for carrying out an assay to measure coagulation time is less than or about 1 hour, 30 minutes, 10 minutes, 5 minutes, or 1 minute.

In some embodiments, obtaining a set of images of a coagulation reaction includes (i) obtaining a set of images of at least one of the plurality of assays and (ii) analyzing the set of images to measure the coagulation time.

In one aspect, a device for measuring coagulation time of a blood sample of a subject is provided. The device comprises (a) a component configured to add a coagulation initiation reagent to the blood sample from the subject under a condition suitable for clot formation, thereby initiating the coagulation reaction, (b) a component configured to obtain a set of images of the coagulation reaction, and (c) a component that analyzes the set of images to measure the coagulation time of the blood sample.

In one aspect, a system for measuring coagulation time of a blood sample of a subject is provided. The system comprises (a) a device configured to add a coagulation initiation reagent to the blood sample from the subject under a condition suitable for clot formation, thereby initiating the coagulation reaction (b) a camera that obtains a set of images of the coagulation reaction, and (c) a computer that analyzes the set of images to measure the coagulation time of the blood sample.

In some aspects, a blood sample that is anticoagulated may be used with any of the assays provided herein. To prepare an anticoagulated blood sample for use with a coagulation assay, a reagent which reverses the effect of an anticoagulant is added in excess over the anticoagulant. For the anticoagulants ethylenediaminetetraacetic acid (EDTA), citrate, and oxalate, a suitable reagent is calcium ($Ca^{2+}$); for the anticoagulant heparin, a suitable reagent is polybrene.

In some embodiments, provided herein is a method of assaying a mixture for coagulation, comprising: initiating a coagulation reaction in a mixture comprising a quantity of an original biological sample, wherein the mixture: i) has a total volume of no greater than 500 microliters, ii) contains no greater than 50 microliters of the original biological sample, and iii) contains no greater than 95% by volume original biological sample; illuminating the mixture and detecting light from the mixture; and analyzing the mixture for coagulation based on an analysis of light from the mixture.

In embodiments, in method provided herein involving a mixture comprising a quantity of an original biological sample, the mixture may have a total volume of no greater than 500, 400, 300, 200, 100 75, 50, 40, 30, 20, 15, 10, 9, 8, 7, 6, 5, 4, 3, 2, 1, 0.5, or 0.1 microliters.

In embodiments, in method provided herein involving a mixture comprising a quantity of an original biological sample, the mixture may contain no greater than 50, 40, 30, 20, 15, 10, 9, 8, 7, 6, 5, 4, 3, 2, 1, 0.5, or 0.1 microliters of the original biological sample.

In embodiments, in method provided herein involving a mixture comprising a quantity of an original biological sample, the mixture may contain no greater than 95%, 90%, 80%, 70%, 60%, 50%, 40%, 30%, 20%, 10%, 5%, 4%, 3%, 2%, 1%, 0.5%, or 0.1% by volume original biological sample.

In embodiments, in methods provided herein involving detecting light from a mixture, detecting light from the mixture comprises obtaining an image of the mixture.

In embodiments, in methods provided herein involving obtaining an image of the mixture, the method further comprises analyzing the image to identify a region of interest (ROI) of the image, wherein the region of interest of the image contains imaged information of the mixture.

In embodiments, in methods provided herein involving identifying a ROI in an image, the method further comprises analyzing the ROI of the image to determine average light intensity in the ROI.

In embodiments, in methods provided herein involving obtaining an image of the mixture, the method comprises obtaining at least a first image and a second image of the mixture over a period of time, wherein a coagulation time of the mixture is determined based on an analysis comprising determining the difference in light intensity in a ROI of the first image and a ROI in the second image.

In embodiments, in methods provided herein involving obtaining an image of a mixture, the image of the mixture is obtained with a CCD or CMOS sensor.

In embodiments, in methods provided herein involving obtaining an image of a mixture, obtaining an image of the mixture comprises obtaining a video of the mixture.

In embodiments, in methods provided herein involving detecting light from a mixture, detecting light from the mixture comprises detecting light transmitted through the mixture.

In embodiments, in methods provided herein involving detecting light transmitted through a mixture, the light transmitted through the mixture is detected over a period of time.

In embodiments, in methods provided herein involving detecting light transmitted through a mixture, a coagulation time of the mixture is identified based on an analysis comprising determining a time when the intensity of light transmitted through the mixture is reduced by a selected amount as compared to a baseline intensity of light transmitted through the mixture.

In embodiments, in methods provided herein involving detecting light transmitted through a mixture, a coagulation time of the mixture is identified based on an analysis comprising determining a time when the intensity of light transmitted through the mixture is reduced by 20% or more as compared to a baseline intensity of light transmitted through the mixture.

In embodiments, in methods provided herein involving detecting light from a mixture, detecting light from the mixture comprises detecting light scattered by the mixture.

In embodiments, in methods provided herein involving detecting light scattered by the mixture, the light scattered by the mixture is detected over a period of time.

In embodiments, in methods provided herein involving detecting light scattered by the mixture, a coagulation time of the mixture is identified based on an analysis comprising determining a time when the intensity of light scattered by the mixture is increased by a selected amount as compared to a baseline intensity of light scattered by the mixture.

In embodiments, in methods provided herein involving detecting light scattered by the mixture, a coagulation time of the mixture is identified based on an analysis comprising determining a time when the intensity of light scattered by the mixture is reduced by 20% or more as compared to a baseline intensity of light scattered by the mixture.

In embodiments, in methods provided herein involving detecting light transmitted through or scattered by the mixture, light transmitted through or scattered by the mixture is detected with a CCD sensor, CMOS sensor, photodiode, or photomultiplier tube (PMT).

In embodiments, in methods provided herein involving a coagulation reaction in a mixture comprising a quantity of an original biological sample, the mixture comprises exogenous fibrinogen. In embodiments, the exogenous fibrinogen may be in the mixture at a concentration of at least 0.1, 0.5, 1, 2, 3, 4, 5, 6, 7, 8, 9, 10, 15, 20, 25, 30, 40, 50, 60, 70, 80, 90, 100, or 150 mg/ml. In embodiments, the exogenous fibrinogen may be in the mixture at a concentration of no more than 0.1, 0.5, 1, 2, 3, 4, 5, 6, 7, 8, 9, 10, 15, 20, 25, 30, 40, 50, 60, 70, 80, 90, 100, 150 or 200 mg/ml. In embodiments, the exogenous fibrinogen may be in the mixture at a concentration of at least 0.1, 0.5, 1, 2, 3, 4, 5, 6, 7, 8, 9, 10, 15, 20, 25, 30, 40, 50, 60, 70, 80, 90, 100, or 150 mg/ml and no more than 0.5, 1, 2, 3, 4, 5, 6, 7, 8, 9, 10, 15, 20, 25, 30, 40, 50, 60, 70, 80, 90, 100, 150, or 200 mg/ml.

In embodiments, in methods provided herein involving a coagulation reaction in a mixture comprising a quantity of an original biological sample, the original biological sample is whole blood. In embodiments, the original biological sample may be whole blood from a subject which has not been diluted by the addition of any liquid to the whole blood after its extraction from the subject.

In embodiments, in methods provided herein involving a coagulation reaction in a mixture comprising a quantity of an original biological sample, the original biological sample is plasma. In embodiments, the original biological sample may be plasma from a subject which has not been diluted by the addition of any liquid to the plasma after its extraction from the subject.

In embodiments, in methods provided herein involving a coagulation reaction in a mixture comprising a quantity of an original biological sample, the mixture is illuminated with a white light source.

In embodiments, in methods provided herein involving a coagulation reaction in a mixture comprising a quantity of an original biological sample, the mixture is illuminated with light of one or more selected wavelengths.

In embodiments, in methods provided herein involving a coagulation reaction in a mixture comprising a quantity of an original biological sample, the mixture is illuminated with light from a light-emitting diode (LED).

In embodiments, an optical signal disclosed herein may be light. In embodiments, an optical signal disclosed herein may be electromagnetic radiation outside of the visual spectrum.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications and patent applications mentioned in this specification are herein incorporated by reference to the same extent as if each individual publication or patent application was specifically and individually indicated to be incorporated by reference. Incorporated publications include U.S. Patent Publication Number 2010/0081144 A1; U.S. Pat. No. 7,888,125; U.S. Patent Publication Number 2011/0093249 A1; U.S. Patent Publication Number 2009/0318775 A1; U.S. Pat. Nos. 7,291,497; 8,012,744; U.S. Patent Publication Number 2006/0264783 A1; U.S. Patent Publication Number 2007/0224084 A1; and U.S. application Ser. No. 13/244,947.

DETAILED DESCRIPTION

Figure 1:
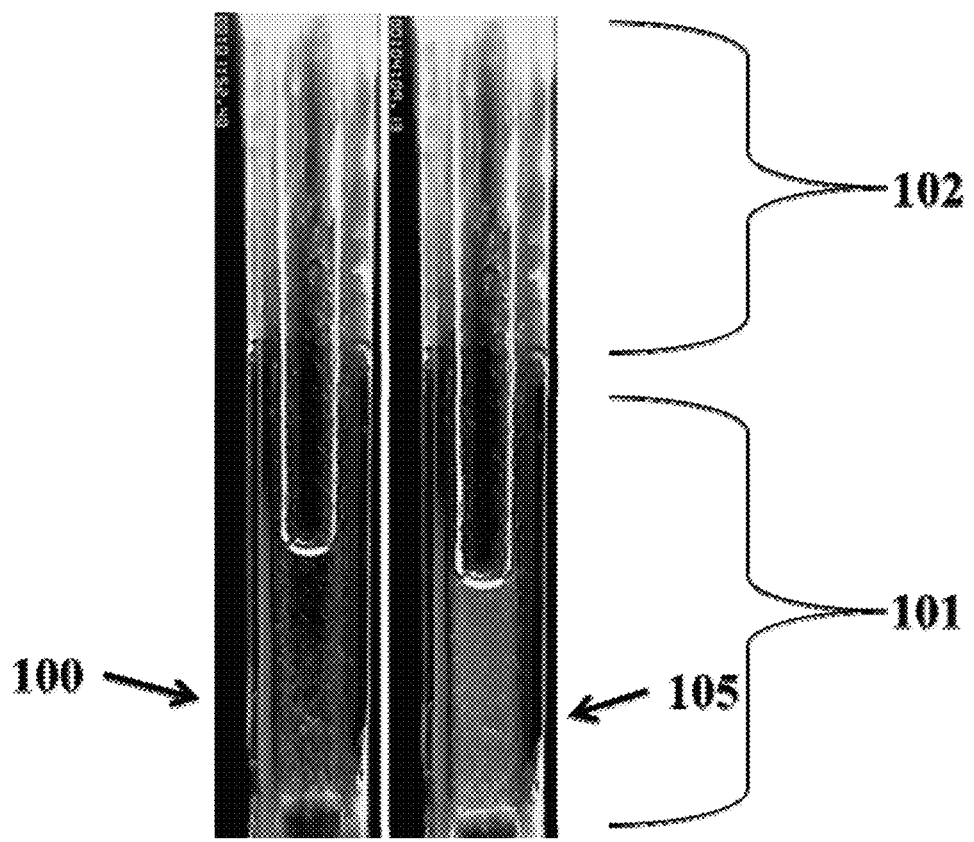
FIG. 1 shows an increase in light scattering from before coagulation (left vessel) to after coagulation (right vessel) of a plasma sample.

Before the embodiments of the invention are described, it is to be understood that such embodiments are provided by way of example only, and that various alternatives to the embodiments of the invention described herein may be employed in practicing the invention. Numerous variations, changes, and substitutions will now occur to those skilled in the art without departing from the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

The articles "a", "an" and "the" are non-limiting. For example, "the method" includes the broadest definition of the meaning of the phrase, which can be more than one method.

A "subject" may be a human or animal. The subject may be living or dead. The subject may be a patient, clinical subject, or pre-clinical subject. A subject may be undergoing diagnosis, treatment, and/or disease prevention. The subject may or may not be under the care of a health care professional.

A "blood sample" is a sample of blood or any blood fraction, blood derivative, and the like. Plasma is an example of a blood fraction. The blood sample can have any suitable volume, be obtained by any suitable method, be collected from any part of the subject at any time, be collected in any suitable vessel, and the like. Blood is a specialized bodily fluid in animals (including humans) that delivers necessary substances such as nutrients and oxygen to the cells and transports metabolic waste products away from those same cells. Blood samples may have any suitable materials added, optionally one or more anti-coagulants. "Blood sample" also includes blood samples that are diluted.

"Plasma" is the liquid component of blood in which the blood cells in whole blood are normally suspended. It is the intravascular fluid part of extracellular fluid (all body fluid outside of cells). It is mostly water (about 93% by volume) and may contain dissolved proteins, glucose, clotting factors, mineral ions, hormones and carbon dioxide (plasma being the main medium for excretory product transportation). Blood plasma may be prepared by spinning (centrifuging) a tube of blood containing an anti-coagulant in a centrifuge until the blood cells sediment to the bottom of the tube. The blood plasma is then aspirated or drawn off.

"Blood serum" is blood plasma without fibrin, fibrinogen or the other clotting factors (i.e., whole blood minus both cells and clotting factors).

Blood samples may be obtained by a "non-venous route", meaning that the blood is not drawn from the veins and arteries of the body with a needle. Non-venous route does not limit the blood sample to being either venous blood (deoxygenated blood) or arterial blood (oxygenated blood). Both venous blood and arterial blood are suitable. Obtaining blood from capillaries of the body is one example of a non-venous route.

A "finger prick", "fingerstick", or similar is one example of a method suitable for obtaining a blood sample by a non-venous route. Here, a sharp point or edge may be used to penetrate the skin of the finger (or any other part of the body), causing blood to emanate from the body. A fingerstick may also be performed on the heel, optionally on the heel of a baby for example. The blood may be collected using a capillary tube, pipette, swab, drop, or any other mechanism known in the art.

The terms "clotting" and "coagulation", as well as their grammatical variants are used interchangeably. They refer to any process in which a fluid or any portion of a fluid solidifies and/or becomes highly viscous. In general, as used herein "clotting" and "coagulation" refer to the biological process by which blood forms clots as described above.

A "coagulation reaction" is any process by which a fluid coagulates, including any process by which blood coagulates. The coagulation reaction may be natural, unmodified, and the like, or may be modified, manipulated, controlled, and the like as described herein.

A "coagulation initiation reagent" is any material added to a blood sample to initiate a coagulation reaction. As described herein, exemplary coagulation initiation reagents include thromboplastin and calcium plus thromboplastin.

The "coagulation time" is the amount of time that elapses between an initiation event such as the addition of a coagulation initiation reagent and the formation of a clot. As described herein, in one version of the assay formation of a clot can be detected by adding beads and observing when they become substantially motionless and/or undergo a transition of mobility.

The terms "beads" and "particles" are used interchangeably to mean small (as described herein), solid elements of matter, suitable for imaging as described herein.

"Substantially motionless" means that the objects such as beads do not move in any direction relative to the coagulation reaction medium (i.e. are suspended in the reaction medium). A small amount of motion is allowable including about 0.01%, about 0.1%, or about 1% of the rate of motion of the beads prior to the coagulation time.

Coagulation time may also extend from an initiation event to a "transition of the mobility" of the beads, generally meaning a deceleration of the movement of the beads.

"Coagulation parameters" are any quantitative or qualitative measure of any property of a coagulation reaction. Coagulation parameters may be relatable to coagulation time as described herein or known in the art.

"Images" are any artifact, for example a two-dimensional picture, set of pictures, or video that has a similar appearance to some physical object. Images may involve the capture of light by a camera.

Images may be "pixilated", meaning that they comprise pixels.

As used herein, "point of service" locations may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein. In some embodiments, a point of service is a point of care. As used herein, a "point of care" refers to any location at or near a subject (e.g. a subject's home or work, grocery stores, drug stores, medical clinics, hospitals, schools, etc.) where a subject may receive medical-related care (e.g. treatment, testing, monitoring, diagnosis, counseling, sample collection, etc.).

"Video" images are a series of images collected sequentially over time. Video images may be collected, for example, at least 1 frame/minute, at least 1 frame/10 seconds, at least 1 frame/second, at least 10 frames/second, at least 20 frames/second, at least 30 frames/second, at least 40 frames/second, at least 50 frames/second, at least 100 frames/second, or at least 200 frames/second.

Coagulation Parameters

Coagulation is highly conserved throughout biology. In mammals, coagulation typically involves both a cellular (platelet) and a protein (coagulation factor) component (although in some circumstances, plasma can clot without platelets being present). The system in humans has been the most extensively researched and is therefore the best understood.

Coagulation begins almost instantly after an injury to the blood vessel has damaged the endothelium lining a vessel. Exposure of the blood to molecules such as tissue factor initiates changes to blood platelets and the plasma protein fibrinogen, a clotting factor. Platelets immediately form a plug at the site of injury. This is typically referred to as primary hemostasis. Secondary hemostasis typically occurs simultaneously. Proteins in the blood plasma, such as coagulation factors or clotting factors, respond in a complex cascade to form fibrin strands, which strengthen the platelet plug. This cascade involves at least about 13 clotting factors, a defect in any of which can result in a coagulation disorder. Furthermore, the coagulation cascade comprises a tissue factor pathway (also known as the extrinsic pathway) and a contact activation pathway (also known as intrinsic pathway). Clinical tests are often designed to eliminate the complexity of the underlying coagulation process and report a single, easily utilized parameter.

In general, coagulation parameters are determined by measuring a "coagulation time", which is the time between initiation of a coagulation event and the formation of a clot. Coagulation parameters encompass the measured coagulation time. In some instances, the coagulation parameter is the coagulation time in the presence of certain reagents, at a certain temperature, and the like.

Numerous tests and/or assays have been developed to assess the function of the coagulation system, any of which may be suitable for measurement using the methods described herein. Common coagulation parameter assays include aPTT, PT, and INR as introduced above and described in more detail below. Other coagulation parameter assays commonly known in the art include fibrinogen testing, which is often performed by the Clauss method, platelet count assays, and platelet function testing which is often performed with a PFA-100™ analyzer from Siemens Corporation. Further coagulation assays and/or clinical procedures known in the art include thrombin clotting time (TCT) testing, bleeding time assays, mixing test (whether an abnormality corrects if the patient's plasma is mixed with normal plasma), coagulation factor assays, antiphosholipid antibody assays, D-dimer test, genetic tests (e.g. factor V Leiden, prothrombin mutation G20210A), dilute Russell's viper venom time (dRVVT) assay, miscellaneous platelet function tests, thromboelastography assays (TEG or Sonoclot), and euglobulin lysis time assays (ELT).

The contact activation (intrinsic) pathway is initiated by activation of the "contact factors" of plasma, and can be measured by the activated partial thromboplastin time (aPTT) test (formerly called the Kaolin cephalin clotting time, "KccT"). The method historically involves collection of blood into a vessel with oxalate or citrate to arrest coagulation by binding calcium. The intrinsic pathway is activated by adding phospholipid, an activator (such as silica, celite, kaolin, ellagic acid), and calcium to reverse the effect of the oxalate or citrate. Time is measured until a clot forms. The test is termed "partial" due to the absence of tissue factor from the reaction mixture.

In certain embodiments, the present method involves dilution of the sample, which may prolong the clotting time of a sample. In embodiments, it may be advantageous to increase the clotting time of a sample by dilution of the sample, for example, in order to increase the time from the initiation of a coagulation reaction with the sample until coagulation of the sample. This may be advantageous, for example, in that it may permit more time for a coagulation to be moved to a light detector, or vice-versa. In another example, it may be advantageous to increase the clotting time of a sample by dilution of the sample in order to provide a larger time frame during with the coagulation time of an assay may be accurately assessed. In embodiments, a diluted sample may be compared with an undiluted sample (e.g. comparison of clotting times) by the preparation of a calibration curve.

An abnormal aPTT time can be indicative of either the presence of a clotting inhibitor or a deficiency in quantity or function of certain clotting factors. Tests can be performed to distinguish the case, wherein the sample is diluted (initially about 50:50) with normal plasma. If the abnormality does not disappear, the sample likely contains an inhibitor such as heparin, antiphospholipid antibodies, or coagulation factor specific antibodies. If the abnormal aPTT time is corrected, there may be a deficiency in factors VIII, IX, XI, XII and/or von Willebrand factor. The present disclosure encompasses both aPTT measurements and mixing tests involving aPTT measurement.

The tissue factor (extrinsic) pathway is initiated by release of tissue factor (a specific cellular lipoprotein), and can be measured by the prothrombin time (PT) test. PT results are often reported as a ratio (INR value) to monitor dosing of oral anticoagulants such as warfarin, indicate liver damage, or indicate vitamin K status. PT measures coagulation factors I, II, V, VII and X. The method historically involves collection of blood into a vessel with citrate and centrifugation to separate blood cells from plasma. Typically, an excess of calcium is added to the EDTA/citrate/oxalate anti-coagulated plasma, tissue factor (also known as factor III) is added, and the time the sample takes to clot is observed. The clotting time can vary substantially according to the analytical system employed and variations between different batches of manufacturer's tissue factor used to perform the test. The INR was devised to standardize the results. As seen in Equation 1, the INR is the prothrombin ratio (prothrombin time for a patient divided by the result for average normal control plasmas) raised to the power of the ISI. The ISI (International Sensitivity Index) indicates how a particular batch of tissue factor compares to an international reference tissue factor. The ISI is usually between 1.0 and 2.0 and is reported by the manufacturer of the tissue factor.

$$INR = \left(\frac{PT_{test}}{PT_{normal}}\right)^{ISI} \quad \text{(Equation 1)}$$

A high INR level such as about 5.0 indicates that there is a high chance of bleeding. A low INR level such as 0.5 indicates that there is a high chance of forming a clot. The normal range for a healthy person is generally between about 0.9 and 1.3. The normal range for persons on warfarin therapy is generally between about 2.0 and 3.0, although the target INR may be higher for those with a mechanical heart valve for example.

Quantitative and qualitative screening of patients for fibrinogen disorders may be achieved by measuring by the thrombin clotting time (TCT). Measurement of the exact amount of fibrinogen present in the blood is generally done using the Clauss method for fibrinogen testing. Many analyzers are capable of measuring a "derived fibrinogen" level from the graph of the Prothrombin time clot. The methods and devices described herein can similarly be used to measure the quantity and/or quality of fibrinogen.

If a coagulation factor is part of the contact activation or tissue factor pathway, a deficiency of that factor will not necessarily affect all coagulation parameter tests. For example, hemophilia A is a deficiency of factor VIII, which is part of the contact activation pathway. Hemophilia A therefore results in an abnormally prolonged aPTT test but a normal PT test. It can be advantageous that the methods and devices described herein allow multiple tests, including various coagulation tests from a single drop of blood in a multiplexed, easy to use format.

Coagulation Measurement Methods, Devices and Systems

The methods, devices and systems described herein may be used to measure any of the above-referenced coagulation parameters and/or monitor the effects of drug dosage in persons medicated with anti-coagulants. Anti-coagulants inhibit clotting and increase the time in which blood clots, and can be used as medication for thrombic disorders or in medical devices. Exemplary anti-coagulants include coumadins such as warfarin, acenocoumarol, phenprocoumon, and phenindione; heparin and its derivative substances such as low molecular weight heparin; synthetic pentasaccharide inhibitors of factor Xa such as fondaparinux and idraparinux; direct thrombin inhibitors including argatroban, lepirudin, bivalirudin, ximelagatran and dabigatran; direct factor Xa inhibitors such as rivaroxaban and apixaban; and other types such as batroxobin and hementin.

In some embodiments, provided herein are methods, devices and systems for measuring coagulation time of a blood sample of a subject. In some embodiments, the methods include adding a coagulation initiation reagent to the blood sample from the subject under a condition suitable for clot formation, thereby initiating the coagulation reaction; obtaining a set of images of the coagulation reaction; and analyzing the set of images to measure the coagulation time of the blood sample. In some embodiments, the methods further include obtaining a blood sample from the subject via a non-venous route.

In one embodiment, a device includes a component capable of adding a coagulation initiation reagent to the blood sample from the subject under a condition suitable for clot formation, thereby initiating the coagulation reaction; a component capable of obtaining a set of images of the coagulation reaction; and a component capable of analyzing the set of images to measure the coagulation time of the blood sample. The component capable of analyzing a set of images to measure the coagulation time of a blood sample may be part of the same apparatus within the device as the component that is configured to obtain more than one image of the coagulation reaction. The component capable of analyzing a set of images to measure the coagulation time of a blood sample may be embedded within the device. The component capable of analyzing a set of images to measure the coagulation time of a blood sample may be configured to perform multiple types of analysis and/or it may be used for multiple applications within the device. A component capable of analyzing a set of images to measure the coagulation time of a blood sample may be located remotely from the device. A component capable of analyzing a set of images to measure the coagulation time of a blood sample may be located in a cloud computing infrastructure (e.g. cloud computing). A component capable of analyzing a set of images to measure the coagulation time of a blood sample may be located in the cloud, and the device may be configured to be dynamically controlled from the cloud. In some embodiments, the device is configured to affect a secondary procedure based on the results of a coagulation assay analysis. In some embodiments, a device capable of performing a coagulation assay as described herein may be configured as a device described in, for example, U.S. Ser. No. 13/244,947, which is herein incorporated by reference in its entirety.

The subject systems may include a device capable of adding a coagulation initiation reagent to the blood sample from the subject under a condition suitable for clot formation, thereby initiating the coagulation reaction; a camera capable of obtaining a set of images of the coagulation reaction; and a computer capable of analyzing the set of images to measure the coagulation time of the blood sample. The computer configured to analyze a set of images to measure the coagulation time of a blood sample may be part of the same apparatus within the system as the camera that is configured to obtain a set of more than one image of the coagulation reaction. The computer configured to analyze a set of images to measure the coagulation time of a blood sample may be embedded within the system. The computer configured to analyze a set of images to measure the coagulation time of a blood sample may be configured to perform multiple types of analysis and/or it can be used for multiple applications within the system. The computer configured to analyze a set of images to measure the coagulation time of a blood sample may be located remotely from a camera configured to obtain a set of more than one image of a coagulation reaction. The computer configured to analyze a set of images to measure the coagulation time of a blood sample may be located in the cloud. The computer configured to analyze a set of images to measure the coagulation time of a blood sample may located in the cloud, and the system may be configured to be dynamically controlled from the cloud. The system may be configured to affect a secondary procedure based on the results of a coagulation assay analysis. In some embodiments, a system capable of performing a coagulation assay as described herein may be configured as a system described in, for example, U.S. Ser. No. 13/244,947, which is herein incorporated by reference in its entirety.

In one aspect, the methods, devices and systems described herein measure coagulation time using small volumes of blood or plasma. The blood can be obtained by a fingerstick, where a drop with a volume of about 20 µL is generally obtained. The coagulation measurement methods described herein can use this entire amount (or even more than 20 µL, including about 2, about 3, or about 4 drops). The methods can also use less than one drop of blood. In some instances, a single drop of blood is used in several measurements, coagulation or otherwise, optionally in a multiplexed format.

The volume of blood or plasma used in the methods, devices and systems described herein can be any suitable amount. In some embodiments, the volume is about 1 ml, about 500 µL, about 400 µL, about 300 µL, about 200 µL, about 100 µL, about 75 µL, about 50 µL, about 40 µL, about 20 µL, about 10 µL, about 9 µL, about 8 µL, about 7 µL, about 6 µL, about 5 µL, about 4 µL, about 3 µL, about 2 µL, about 1 µL, about 0.8 µL, about 0.6 µL, about 0.4 µL, about 0.2 µL, about 0.1 µL, about 0.05 µL, about 0.01 µL, and the like. In some embodiments, the volume is at most about 1 ml, at most about 500 µL, at most about 400 µL, at most about 300 µL, at most about 200 µL, at most about 100 µL, at most about 75 µL, at most about 50 µL, at most about 40 µL, at most about 20 µL, at most about 10 µL, at most about 9 µL, at most about 8 µL, at most about 7 µL, at most about 6 µL, at most about 5 µL, at most about 4 µL, at most about 3 µL, at most about 2 µL, at most about 1 µL, at most about 0.8 µL, at most about 0.6 µL, at most about 0.4 µL, at most about 0.2 µL, at most about 0.1 µL, at most about 0.05 µL, at most about 0.01 µL, and the like. In embodiments, methods provided herein may be performed wherein no more than 200 µL, 100 µL, 75 µL, 50 µL, 40 µL, 20 µL, 10 µL, 9 µL, 8 µL, 7 µL, 6 µL, 5 µL, 4 µL, 3 µL, 2 µL, 1 µL, 0.8 µL, 0.6 µL, 0.4 µL, 0.2 µL, 0.1 µL, 0.05 µL, 0.01 µL, 0.005 µL, or 0.001 µL of original (undiluted) sample is used to perform the method.

In such embodiments, methods provided herein may be performed with a low volume of the total reaction mixture. For example, methods provided herein may be performed where the total volume of the reaction mixture is 200 µL, 100 µL, 75 µL, 50 µL, 40 µL, 20 µL, 10 µL, 9 µL, 8 µL, 7 µL, 6 µL, 5 µL, 4 µL, 3 µL, 2 µL, 1 µL, 0.8 µL, 0.6 µL, 0.4 µL, 0.2 µL, 0.1 µL, 0.05 µL, 0.01 µL, 0.005 µL, or 0.001 µL. Within the total volume of a reaction mixture, any volume of original (undiluted) sample disclosed herein as sufficient for performing a method (e.g. no more than 200 µL, 100 µL, etc.) may be present.

In some embodiments, the device or system includes a microscope and/or camera. The camera may be a video camera. The microscope may be configured for brightfield, darkfield, or fluorescence microscopy. The device or system may be further configured to receive a cartridge. The cartridge may contain a blood sample and/or reagents for performing coagulation assays. The device or system may contain integrated sample processing mechanisms and/or the device or system may have automated sample processing mechanisms. In some aspect, the device or system may be configured to receive a cartridge containing a blood sample and to perform an automated coagulation assay.

In some embodiments, a user may introduce a volume of blood sample from a subject into a cartridge. The volume of blood may be a small amount, such as 1 ml or less, 500 µL or less, 400 µL or less, 300 µL or less, 200 µL or less, 100 µL or less, 75 µL or less, 50 µL or less, 40 µL or less, 30 µL or less, 20 µL or less, 15 µL or less, 10 µL or less, 9 µL or less, 8 µL or less, 7 µL or less, 6 µL or less, 5 µL or less, 4 µL or less, 3 µL or less, 2 µL or less, 1 µL or less, 0.8 µL or less, 0.6 µL or less, 0.5 µL or less, 0.4 µL or less, 0.3 µL or less, 0.2 µL or less, or 0.1 µL or less. The cartridge may contain an anticoagulant which mixes with the blood sample. The cartridge may be introduced into a device. In embodiments, an anticoagulant may be mixed with a blood sample before the blood sample is introduced into the cartridge. Either within the cartridge or within the device, the blood sample may be separated into a plasma portion and packed portion containing red blood cells. Alternatively, the blood sample may remain whole blood. The blood sample may be distributed within the device to one or more different assay units, and used for one or more different assays. The blood sample may be distributed within the device by a fluid transfer device. The blood sample may be diluted. The blood sample may be mixed with one or more reagents. The reagents may perform one or more of the following functions: A) reverse the effect of an anticoagulant (for example, addition of calcium ions to a sample containing EDTA may reverse the anti-coagulant effects of EDTA); B) promote coagulation of the sample (for example, phospholipid, silica, celite, kaolin, ellagic acid, etc.); C) facilitate visualization of the coagulation reaction (for example, small beads or other particles which may be observed); D) increase the strength and/or mass of a coagulation clot (for example, fibrinogen); or E) reduce non-specific binding of analytes of a blood sample within reaction vessels (for example, detergents or proteins). The reagents may perform additional functions, as well. The reagents may be in liquid or dry form. Reagents such as sucrose, trehalose, polyethylene glycol, or albumin may be formulated in any of a variety of dry forms, such as in an erodible film formulated for rapid dissolution. The mixture of blood sample with reagents may be observed by any device capable of obtaining one or more image correlated with the coagulation reaction. Video images may be obtained. Images of the coagulation reactions may be analyzed, in order to determine the coagulation time of the reaction. Analysis a coagulation reaction may be performed with the aid of a computer or other component of the device. The coagulation time of the reaction may then be used in the analysis of the medical condition of a subject. One or more the steps of the method may be performed at point of service or point of care location. Performance of methods disclosed herein a point of care location may enable medical personnel to rapidly make a treatment decision for a subject based on assay data related to the specific subject.

Sample Handling and Reaction Chambers

Samples, reagents, and coagulation assays described herein can be handled and contained by a variety of reaction vessel types. A sample handing device and a reaction vessel can be, for example, a well, a tube, an open ended tip, which may also be a cuvette, or rectangular or square section capillaries. As used herein, a tip can also be referred to as a sample tip, a cuvette tip, a reaction chamber, a cuvette, a capillary, a sample handing device, or a sample transfer device. Samples may be collected from a source into a tip or a tube. The tips may be sealed. Such seals may be permanent or reversible. Once the assay is ready for reading, the coagulation reaction can be presented to an optical system for image analysis or other types of reading. Many assays can be processed in parallel. In embodiments, a reaction vessel can contain multiple separate fluidically isolated cavities, such that multiple different assay reaction mixtures can be supported in the same reaction vessel. Assay readout can be serial or simultaneous depending on the assay protocol and/or incubation time. For assays involving measurement of a rate of change, the assay element can be presented to the optical system more than once at different times.

Fluid and Material Handling Devices

A fluid transfer apparatus can be part of a device. A fluid transfer device can be part of a system. The fluid transfer device or apparatus can comprise a plurality of heads. Any number of heads may be part of the fluid transfer device. In an example, a fluid transfer device has about eight heads mounted in a line and separated by a distance. In an embodiment, the heads have a tapered nozzle that engages by press fitting with a variety of tips. The tips can have a feature that enables them to be removed automatically by the instrument and disposed into in a housing of a device after use. In an embodiment, the assay tips are clear and transparent and can be similar to a cuvette within which an assay is run that can be detected by an optical detector such as a photomultiplier tube or camera sensor.

In an example, a programmable processor of a system can comprise instructions or commands and can operate a fluid transfer device according to the instructions to transfer liquid samples by either withdrawing (for drawing liquid in) or extending (for expelling liquid) a piston into a closed air space. Both the volume of air moved and the speed of movement can be precisely controlled, for example, by the programmable processor.

Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion. Removal of samples and reagents can be achieved by expelling the liquid into a reservoir or an absorbent pad in a device. Another reagent can then be drawn into the tip according to instructions or protocol from the programmable processor.

A system can comprise a holder or engager for moving the assay units or tips. An engager may comprise a vacuum assembly or an assembly designed to fit snugly into a boss of an assay unit tip. For example, a means for moving the tips can be moved in a manner similar to the fluid transfer device heads. The device can also be moved on a stage according to the position of an engager or holder.

In an embodiment, an instrument for moving the tips is the same as an instrument for moving a volume of sample, such as a fluid transfer device as described herein. For example, a sample collection tip can be fitted onto a pipette head according to the boss on the collection tip. The collection tip can then be used to distribute the liquid throughout the device and system. After the liquid has been distributed, the collection tip can be disposed, and the pipette head can be fitted onto an assay unit according to the boss on the assay unit. The assay unit tip can then be moved from reagent unit to reagent unit, and reagents can be distributed to the assay unit according to the aspiration- or pipette-type action provided by the pipette head. The pipette head can also perform mixing within a collection tip, assay unit, or reagent unit by aspiration- or syringe-type action.

In another embodiment, tips containing liquids including coagulation assays can be disconnected from the pipetting device and "parked" at specific locations within the instrument or within a disposable unit. If needed, tips can be capped using a seal to prevent liquids from draining out. In some embodiments, the seal can be a vinyl seal. Any variations in the fluid and material handling devices disclosed herein or described in U.S. Ser. No. 13/244,947 or U.S. Pat. No. 8,088,593 which are incorporated herein in their entirety, can be adopted Exemplary Sample Tips A variety of container shapes can be utilized as sample tips, reaction chambers, capillaries and cuvettes. For example, a cuvette can be circular, cylindrical, square, rectangular, cubical, conical, pyramidal, or any other shape capable of holding a sample of fluid. Rectangular cuvettes where a light beam impinges at right angles or other angle (other than 0 degrees) to the light beam to the cuvette surfaces can be employed. In such rectangular cuvettes, the liquid sample that is illuminated is also rectangular and is defined by the cuvette. Cuvettes with circular cross-sections can also be used.

Variable pathlength cuvettes can be used to optimize and extend the assay response and minimize the volume of sample required to measure the assay. Cuvettes can be longer in relation to their cross-section in at least one region.

In some embodiments, one version of the assay cuvette has a circular cross-section in the direction of the light beam. The use of a cuvette with a circular cross-section may have several advantages, including, but not limited to the following:

1. The optical pathlength can be precisely defined. Dimensional precision of injection-molded parts have been found to be better than 1-2% Coefficient of Variation (CV). In conventional microtiter plates the unconstrained liquid meniscus can introduce imprecision in pathlength.

2. The open-ended character and circular section of the tips confers excellent fluid handling characteristics, making aspiration of liquids very precise.

3. The optical image of the tips provides for the ability to identify the tip location and boundaries of the liquid column and to locate very precisely the center of the tip where the signal is maximal.

4. More than one liquid sample can be incubated and analyzed in the same tip. This is because in the narrow part of the tip, very little material transfer occurs (in the axial direction) between adjacent "slugs" of liquid.

Any variations in cuvettes or imaging systems or methods disclosed herein or described in U.S. Ser. No. 13/355,458 which is incorporated herein in its entirety, can be adopted.

An exemplary tip may have the following general features:

Tip length: 0.5-4 cm.
Tip outer diameter: 0.2-1.0 cm.
Tip inner diameter: 0.1-0.5 cm.
Tip capacity for liquids: 0.5-50 uL.
Tip dimensional precision: generally better than 2% or +/−0.001 cm.

Tip configuration: The tip will generally have a feature that engages with a pipette (cylindrical) so as to form a fluid tight seal. There is a region generally cylindrical or conical which is used for imaging. The lower end of the tip will typically be narrow so as to aid in retention of vertical liquid columns under gravity.

Tip material: Preferably clear plastic (polystyrene, polypropylene etc.) (for example, which transmits light in the visible >80, 60, 40, 20%). Other suitable materials are not excluded.

In one example, at the upper end of the cylinder is a truncated cylindrical "boss" fluidically connected to the cylinder and adapted so as to be able to engage with the tapered feature of a pipetter. The lower end of the tip may be narrowed to provide a feature that enables the tip to hold its liquid contents when oriented vertically and not attached to the pipetter. The external shape of the lower end of the tip is typically also somewhat pointed with the diameter being reduced from the main part of the cylindrical shaft toward the end so as to be capable of being fluidically sealed with a flexible (vinyl) cap into which the tip end is press fit. Tips are usually made of molded plastic (polystyrene, polypropylene and the like). The tips can be clear or translucent such that information about the sample can be acquired by imaging.

In some embodiments, the tip is configured with (1) an upper feature that can engage to form an air tight seal with a pipette head, (2) a basically cylindrical (or conical with a very slight draft angle) shaft and a narrow, pointed lower tip. This tip can form a liquid-tight seal with a cap. The pointed shape aids in getting good conformance with the cap under moderate force. The tip material may be injection-molded polystyrene.

Sealing can be achieved using a cap made of vinyl or other materials which is easily press-fitted to the narrow end of the sample containment means using force generated by motion of the instrument stage in the z-direction.

Reagents and Reactions

Any user may perform the methods described herein. The user can be the subject himself or herself. The user can be a medically trained person such as a doctor or nurse, but this is not necessarily required. The user may have undergone general or special technical training in order to perform the methods described herein, but this is not necessarily required. The methods may also be performed by more than one user, for example various users may perform various steps.

The methods described herein may begin with a previously drawn blood and/or plasma sample. In such embodiments, the sample will often have an anticoagulant added, typically EDTA. The methods described herein may also begin with obtaining blood from a subject. The blood may be obtained from a non-venous route (e.g. from capillaries, e.g. not involving a needle). The blood may be obtained from a finger-stick, for example. The blood may be collected into any suitable vessel. In some embodiments, the blood is collected into a cartridge. The vessel and/or collection cartridge may contain an anticoagulant, typically EDTA. The anticoagulant may spontaneously mix with and/or dissolve in the blood sample.

In some embodiments, the sample (generally containing an anticoagulant) is centrifuged. Centrifugation may be performed for any suitable combination of time and centrifugal force such that the blood separates into packed formed elements and plasma. The formed elements generally consist predominantly of red blood cells and the plasma is generally substantially free of cells. Centrifugation is not always necessary. Some embodiments can be performed with whole blood. The whole blood may be diluted. Some embodiments may also prepare plasma from blood without the use of centrifugation, such as by addition of a reagent that aggregates blood cells for example.

All or a portion of the plasma may be used in the assay. The plasma may also be distributed among several assays in a multiplexed format. Suitable methods for pipetting low volumes of plasma are disclosed in, for example, U.S. Ser. No. 13/244,947 and U.S. Pat. No. 8,088,593. In some embodiments, the plasma is diluted as described below. The plasma can be diluted in any suitable fluid. Exemplary fluids include HEPES buffered saline (HBS), phosphate buffered saline (PBS), tris buffered saline (TBS), and solutions which contain imidazole, ethylenediamine, N-ethyl morpholine, triethanlolamine, or other buffering agents in the neutral range (i.e. about pH 5-9). The plasma and/or plasma sample may be diluted any one or more of before, during, or after measuring the coagulation parameter and/or distributing the plasma among the assays of a multiplexed format.

A small volume of the optionally diluted sample is then mixed with certain reagents. This mixing is generally performed rapidly, such as in less than about 10 seconds, less than about 5 seconds, or less than about 1 second. The reagents generally include (a) if needed, a reagent which reverses the effect of the anti-coagulant, (b) a reagent which promotes coagulation, and (c) for diluted samples one or more ancillary reagents such as fibrinogen, or proteins as described below. In some instances, a dispersion of fluorescent or other particles may be added to determine coagulation time by imaging as described below.

The reagent that reverses the effect of the anti-coagulant can be any suitable reagent. For example, calcium ions may be added to reverse the effect of EDTA. The calcium ions, optionally in the form of $CaCl_2$, may be added in excess. In embodiments, calcium may be added to coagulation reactions provided herein such that the final concentration of calcium ions ($Ca^{2+}$) in the reaction is at least 0.01, 0.05, 0.1, 0.2, 0.3, 0.4, 0.5, 1, 2, 3, 4, 5, 10, 15, 20, 25, 50, 75, or 100 mg/ml, no more than 0.01, 0.05, 0.1, 0.2, 0.3, 0.4, 0.5, 1, 2, 3, 4, 5, 10, 15, 20, 25, 50, 75, or 100 mg/ml, or between 0.01, 0.05, 0.1, 0.2, 0.3, 0.4, 0.5, 1, 2, 3, 4, 5, 10, 15, 20, 25, 50, or 75 mg/ml and 0.05, 0.1, 0.2, 0.3, 0.4, 0.5, 1, 2, 3, 4, 5, 10, 15, 20, 25, 50, 75, or 100 mg/ml.

The reagents that promote coagulation ("coagulation initiation reagent") can vary depending on the coagulation parameter being measured. As described above, measurement of PT and/or INR involves the addition of prothrombin reagent comprising tissue factor and lipids. The aPTT assay uses phospholipid plus an activator such as silica, celite, kaolin or ellagic acid.

In some embodiments, one or more of the reagents are present in concentrated or dried form. Concentrated reagents may reduce the amount of sample dilution. Regarding dried reagents, mixing the sample with the dried reagents rapidly dissolves and/or disperses the reagents in the sample. The dried reagents may be dissolved and/or dispersed in the sample by repeated aspiration or other means of mixing. Any reagent may be concentrated or dried, provided that the reagent is stable in concentrated or dried form. In fact, some reagents may have increased stability in dried form, potentially avoiding the need for refrigeration, preservatives and the like. In particular, the PT reagent, aPTT reagent, and/or $CaCl_2$ may be concentrated and/or dried. All of the reagents can be combined into one dried reagent. For example, the reagents can be in the form of an erodible film formulated for rapid dissolution including formulations with sucrose, trehalose, polyethylene glycol, albumin, and the like. One formulation of dried reagents suitable for use in PT and/or INR measurement can be found in U.S. Pat. No. 5,164,598.

In some embodiments, the plasma mixed with reagents is then incubated, generally at a controlled temperature. In some embodiments, the temperature is about 15° C., about 20° C., about 25° C., about 30° C., about 35° C., about 40° C., about 45° C., about 50° C., and the like. In some embodiments, the temperature is between about 15° C. and about 50° C., between about 30° C. and about 40° C., and the like. In some instances the incubation step may be omitted. For example, the aPTT assay may not require incubation.

Methods of Dilution

In some embodiments, the blood or plasma sample is diluted. Diluting the sample may confer at least three potential advantages. First, dilution may reduce the amount of sample required. In some embodiments, once an aliquot of diluted plasma has been reserved for measurement of coagulation parameters, the remainder can be used for other assays. Also, for example, dilution of the sample 10-fold allows the method to use 10-fold less sample. Secondly, dilution may reduce light scattering from lipemic samples (samples with a high fat content that may appear milky white). Thirdly, dilution increases the coagulation time. This may be advantageous in making the assay less time-sensitive. That is, steps such as mixing the sample with reagents or moving the camera do not have to be performed so rapidly. Performing such steps can be particularly challenging when using small sample volumes where flow is laminar, the camera has to be aligned to a small volume, and the like.

The coagulation time may be any suitable time, optionally long enough to make the procedure less time sensitive and more precise and/or accurate, and optionally short enough to be performed at the point of care and give near real-time results. In some embodiments, the coagulation assay is performed in parallel (i.e. multiplexed) with measurement of other biomarkers or therapeutic agents. In these embodiments, it may be advantageous and/or practical to dilute the sample such that the coagulation time is similar to the other measurement times being performed in the multiplexed assay. Optionally the coagulation time is similar to or shorter than the longest of the other biomarker or therapeutic agent assays.

In some embodiments, the coagulation time, using either diluted or non-diluted sample, is about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, and the like. In some embodiments, the coagulation time, using either diluted or non-diluted sample, is less than about 1 minute, less than about 2 minutes, less than about 3 minutes, less than about 4 minutes, less than about 5 minutes, less than about 6 minutes, less than about 7 minutes, less than about 8 minutes, less than about 9 minutes, less than about 10 minutes, less than about 15 minutes, less than about 20 minutes, less than about 25 minutes, less than about 30 minutes, and the like. In some embodiments, the coagulation time, using either diluted or non-diluted sample, is between about 1 minute and about 2 minutes, between about 1 minute and about 5 minutes, between about 2 minutes and about 10 minutes, between about 5 minutes and about 8 minutes, and the like.

The sample may be diluted to any suitable extent, optionally diluted to achieve any suitable coagulation time. In some embodiments, the sample is diluted by about 1.2 fold, about 1.5 fold, about 2 fold, about 3 fold, about 4 fold, about 5 fold, about 7.5 fold, about 10 fold, about 20 fold, about 30 fold, about 40 fold, about 50 fold, or about 100 fold. In some embodiments, the sample is diluted by at least about 1.2 fold, at least about 1.5 fold, at least about 2 fold, at least about 3 fold, at least about 4 fold, at least about 5 fold, at least about 7.5 fold, at least about 10 fold, at least about 20 fold, at least about 30 fold, at least about 40 fold, at least about 50 fold, or at least about 100 fold. In some embodiments, the sample is diluted by at most about 1.2 fold, at most about 1.5 fold, at most about 2 fold, at most about 3 fold, at most about 4 fold, at most about 5 fold, at most about 7.5 fold, at most about 10 fold, at most about 20 fold, at most about 30 fold, at most about 40 fold, at most about 50 fold, or at most about 100 fold. In some embodiments, the sample is diluted by between about 1.2 fold and about 2 fold, between about 2 fold and about 5 fold, between about 5 fold and about 20 fold, or between about 5 fold and about 50 fold. In embodiments, a sample may be diluted to contain original sample at a concentration (by volume) of 90% or less, 80% or less, 70% or less, 60% or less, 50% or less, 40% or less, 30% or less, 20% or less, 10% or less, 5% or less, 4% or less, 3% or less, 2% or less, 1% or less, 0.5% or less, 0.1% or less, 0.05% or less, 0.01% or less, 0.005% or less, or 0.001% or less original sample (i.e. as used herein, a diluted sample which contains original sample at a concentration of 80% or less will contain, in an exemplary total volume of diluted sample of 100 ul, no more than 80 ul of the original (undiluted) sample; similarly, a diluted sample which contains original sample at a concentration of 2% or less will contain, in an exemplary total volume of diluted sample of 100 ul, no more than 2 ul of the original (undiluted) sample). The original sample may be, for example, neat whole blood or plasma. In embodiments, a coagulation reaction may contain diluted sample such that the final concentration (by volume) of original sample in the reaction is 90% or less, 80% or less, 70% or less, 60% or less, 50% or less, 40% or less, 30% or less, 20% or less, 10% or less, 5% or less, 4% or less, 3% or less, 2% or less, 1% or less, 0.5% or less, 0.1% or less, 0.05% or less, 0.01% or less, 0.005% or less, or 0.001% or less original sample in the reaction mixture (i.e. a coagulation reaction which contains original sample in the reaction at a concentration of 80% or less will contain, in an exemplary total volume of the reaction of 100 ul, no more than 80 ul of the original (undiluted) sample; similarly, a coagulation reaction which contains original sample at a concentration of 2% or less will contain, in an exemplary total volume of the reaction of 100 ul, no more than 2 ul of the original (undiluted) sample).

In some embodiments, it may be desirable to complete the entire coagulation assay in a short time, as a short time may be desirable for using the assay at the point of care in order to achieve a near real-time result. The total assay time may extend from drawing blood, optionally by a finger-stick to adding certain reagents to the blood to capturing images to analyzing images to reporting a coagulation parameter. The total assay time may also extend to using the reported coagulation parameter to calculate and/or administer a dose of anti-coagulant to a patient in need thereof. In some embodiments, the total assay time is about 1 minute, about 3 minutes, about 5 minutes, about 10 minutes, about 15 minutes, about 20 minutes, about 30 minutes, and the like. In some embodiments, the total assay time is less than about 1 minute, less than about 3 minutes, less than about 5 minutes, less than about 10 minutes, less than about 15 minutes, less than about 20 minutes, less than about 30 minutes, and the like.

In some embodiments, dilution of the sample under certain conditions may reduce the mechanical strength of the clot and/or turbidity of the sample upon coagulation. In certain instances this may be disadvantageous if the clot strength is decreased such that it becomes difficult to determine the time at which clotting occurs. The present disclosure encompasses a number of optional methods for compensating for dilution.

In some embodiments, the method may be performed in small containers and/or containers that have a high surface area to volume ratio. This may aid in adhesion of an incipient clot to the surface of the container. Container size and/or surface area may be a consideration in embodiments where coagulation time is determined by imaging bulk reciprocating movement of the sample as described below. The volume of the container and/or surface area to volume ratio of the container may be any suitable value such that the methods described herein can be reliably and accurately performed.

In some embodiments, ancillary reagents may be added such as small particles, fibrinogen, surfactants, and/or proteins. Such ancillary reagents may support the formation of a stronger clot and/or may increase sample turbidity upon coagulation.

In some embodiments, small particles may be added to the sample to visualize changes in sample viscosity. A reduction in movement of the small particles may be correlated with an increase in sample viscosity, and may provide an indication of sample coagulation.

Without being held to any particular theory, it is believed that in many versions of the present methods gravitational force is too weak to overcome the viscous resistance to movement of the particles once coagulation has occurred, even for coagulation in dilute samples. Imaging of the particles may be used to determine coagulation time as described herein.

In some embodiments, fibrinogen may be added to the sample. Additional fibrinogen can provide for a more substantial clot and/or provide for increased turbidity when a clot forms. The fibrinogen is optionally derived from animals, optionally being bovine fibrinogen. The amount of fibrinogen to add can be any amount such that a clot of suitable mechanical strength and/or turbidity is formed. In various embodiments, the diluted sample is supplemented with about 1 mg/mL, about 2 mg/mL, about 3 mg/mL, about 4 mg/mL, about 5 mg/mL, or about 10 mg/mL fibrinogen. In various embodiments, the diluted sample is supplemented with at least about 1 mg/mL, at least about 2 mg/mL, at least about 3 mg/mL, at least about 4 mg/mL, at least about 5 mg/mL, or at least about 10 mg/mL fibrinogen. In embodiments, coagulation reactions provided herein may be supplemented with extrinsic fibrinogen such that the final concentration of the extrinsic fibrinogen in the coagulation reaction is at least 0.01, 0.05, 0.1, 0.2, 0.3, 0.4, 0.5, 1, 2, 3, 4, 5, 10, 15, 20, 25, 50, 75, or 100 mg/ml, no more than 0.01, 0.05, 0.1, 0.2, 0.3, 0.4, 0.5, 1, 2, 3, 4, 5, 10, 15, 20, 25, 50, 75, or 100 mg/ml, or between 0.01, 0.05, 0.1, 0.2, 0.3, 0.4, 0.5, 1, 2, 3, 4, 5, 10, 15, 20, 25, 50, or 75 mg/ml and 0.05, 0.1, 0.2, 0.3, 0.4, 0.5, 1, 2, 3, 4, 5, 10, 15, 20, 25, 50, 75, or 100 mg/ml.

In embodiments, a coagulation reaction may contain diluted sample such that the final concentration of original sample (e.g. neat plasma or whole blood) in the reaction is 80% or less, 70% or less, 60% or less, 50% or less, 40% or less, 30% or less, 20% or less, 10% or less, 5% or less, 4% or less, 3% or less, 2% or less, 1% or less, 0.5% or less, 0.1% or less, 0.05% or less, 0.01% or less, 0.005% or less, or 0.001% or less, and the coagulation reaction may further contain extrinsic fibrinogen such that the final concentration of the extrinsic fibrinogen in the coagulation reaction is at least 0.01, 0.05, 0.1, 0.2, 0.3, 0.4, 0.5, 1, 2, 3, 4, 5, 10, 15, 20, 25, 50, 75, or 100 mg/ml, no more than 0.01, 0.05, 0.1, 0.2, 0.3, 0.4, 0.5, 1, 2, 3, 4, 5, 10, 15, 20, 25, 50, 75, or 100 mg/ml, or between 0.01, 0.05, 0.1, 0.2, 0.3, 0.4, 0.5, 1, 2, 3, 4, 5, 10, 15, 20, 25, 50, or 75 mg/ml and 0.05, 0.1, 0.2, 0.3, 0.4, 0.5, 1, 2, 3, 4, 5, 10, 15, 20, 25, 50, 75, or 100 mg/ml.

It is also possible to use other methods to compensate for dilution and/or to use the methods described herein in combination with each other or in combination with other methods. For example, one can add fibrinogen and particles in order to aid in the determination of coagulation time in diluted samples. As discussed elsewhere herein, in embodiments, various advantages may be conferred by the use of diluted samples for coagulation assays. Accordingly, use of fibrinogen or other reagents to compensate for dilution of a sample may permit the advantages associated with the use of diluted samples in coagulation assays to be realized, while still achieving effective and measurable coagulation of the diluted sample.

In some instances, dilution of blood and/or plasma samples may lead to loss of clotting factors from the sample, for example by adsorption to surfaces such as tubes or pipette tips. In some embodiments, surfactants and/or proteins may be added to the sample to prevent and/or reduce the loss of clotting factors. An exemplary surfactant suitable for this purpose is Triton X-100. An exemplary protein suitable for this purpose is bovine serum albumin (BSA). The concentration of surfactant and/or protein may be any suitable concentration such that clotting factor loss is reduced to any acceptable level.

Images

The devices and systems described herein may include any imaging devices, such as a camera, CCD sensor-containing device, CMOS sensor-containing device or any other handheld, benchtop, or larger devices with imaging capabilities. The methods described herein may use optical methods to measure a coagulation parameter. In some embodiments, coagulation of the sample increases the turbidity and light scattering of the sample. The addition of fibrinogen is one method for increasing the turbidity and light scattering of the clot such that it can be detected as described herein.

In other embodiments, the sample is initially turbid and/or is made to be initially turbid by addition of suspended particles often individually invisible to the naked eye but producing a turbid haziness in bulk. An initially turbid sample may become less turbid over time as the particles settle from the bulk fluid, but coagulation of the sample may halt or substantially slow the settling of particles and/or decrease in turbidity. In some embodiments, coagulation time can be determined by the cessation or slowing of the rate of decrease in bulk turbidity of the sample. The determination of coagulation time by turbidity is an optical technique (involves light) and may involve capture of images, but does not necessarily require the use of images. For example, in embodiments, turbidity may be measured by measuring absorbance of light through a sample or scattering of light by a sample, either of which may be sensed, for example with a photomultiplier tube or a photodiode. In some embodiments, images obtained with methods herein are light scattering images, and are optionally not pixilated. Having a long path of light through the sample, or increasing the sample path length is one means for increasing the sensitivity of measurements involving changes in turbidity.

The methods described herein may use images to measure a coagulation parameter. The images can be video images or a time set of photographic images. The images may be captured by optical devices such as cameras, mirrors, lenses, microscopes, and the like. The images can be two-dimensional or three-dimensional. The images can be black and white, gray-scale or color. The images can be digital or analog, including digitization of analog images. The images can be pixilated, meaning that it comprises a plurality of pixels which may distinguish the images from other optical phenomena including various forms of spectroscopy. A two dimensional image may be pixilated by dividing the image into a plurality of rows and columns, wherein each element (row and column position) defines a pixel.

The images can be pixilated into any suitable number of pixels. In one embodiment, the image is divided into 512 rows and 512 columns, defining 262,144 pixels. In some embodiments, the image comprises about 10,000 pixels, about 50,000 pixels, about 60,000 pixels, about 100,000 pixels, about 200,000 pixels, about 500,000 pixels, about 1,000,000 pixels, about 5,000,000 pixels, about 10,000,000 pixels, or about 50,000,000 pixels. In some embodiments, the image comprises at least about 10,000 pixels, at least about 50,000 pixels, at least about 60,000 pixels, at least about 100,000 pixels, at least about 200,000 pixels, at least about 500,000 pixels, at least about 1,000,000 pixels, at least about 5,000,000 pixels, at least about 10,000,000 pixels, or at least about 50,000,000 pixels. In some embodiments, a pixel density and/or resolution may be reported in which a given area comprises a certain number of pixels.

In one aspect, the method describes determining a coagulation time using a time series of images. Images can be captured at any suitable rate. The rate can be constant, or can vary over the time course of coagulation, optionally with more images being captured around the time when the clot forms in the sample. In some embodiments, images are captured at a rate of about 1 frame per second, about 5 frames per second, about 10 frames per second, about 15 frames per second, about 20 frames per second, about 30 frames per second, about 50 frames per second, about 100 frames per second, about 500 frames per second, and the like. In some embodiments, images are captured at a rate of at least about 1 frame per second, at least about 5 frames per second, at least about 10 frames per second, at least about 15 frames per second, at least about 20 frames per second, at least about 30 frames per second, at least about 50 frames per second, at least about 100 frames per second, at least about 500 frames per second, and the like. In some embodiments, interpolation methods can be used to estimate a coagulation time that falls between frame captures.

The images can be stored on a computer readable medium. The images can be processed in real-time or processed at a later time. The images can be processed manually or using methods implemented by a computer.

Optical Setup for Coagulation Analysis

Coagulation analysis can be performed using an optical setup. The optical setup may include, without limitation a light source and a light detector. Typically, the light source provides light which reaches the coagulation reaction, and the detector detects light from the reaction (e.g. light scattered by, reflected by, or transmitted through the reaction).

The light source can be, for example, one or more white light sources, single color LEDs, broad frequency light from fluorescent lamps or LEDs, LED arrays, mixtures of red, green, and blue light sources, phosphors activated by an LED, fluorescent tubes, incandescent lights, lasers, or arc sources, such as a flash tube.

A variety of light detectors can be used with methods and systems provided herein. In embodiments, an image sensor such as a CCD sensor or CMOS sensor may be used. An image sensor may be provided as part of a camera. A camera may include an aperture or lens. In embodiments, the lens of a camera may have a focal length of anywhere from 5-100 mm, including 35 mm. The lens may be glass with a standard object distance or may be a webcam lens. In embodiments, light detectors may be a photon counter/detector such as a photomultiplier tube (PMT) or photodiode (including, for example, avalanche photodiodes, wide range photodiodes, pin photodiodes, and single frequency photodiodes). In some embodiments a pin diode can be coupled to an amplifier to create a detection device with sensitivity comparable to a PMT. A detector can also comprise a light source, such as a bulb or light emitting diode (LED). The light source can illuminate an assay in order to detect the results. The detector can also comprise optics to deliver the light source to the assay, such as a lens or fiber optics.

The light source and detector may have a variety of configurations relative to each other and to the coagulation reaction support (e.g. vessel, surface, tube, tip, etc.). For example, the light source and detector may both be in-line with the reaction support, or one or both of the light source and detector may be at angle relative to the reaction support or each other. In an example, the light source is in-line with coagulation reaction support, and the detector is at a 90 degree angle relative to the reaction support. There may be an aperture between the light source or reaction support and the detector. Images of a reaction may be taken when a reaction support is moved into an optical pathway, such that light from the light source reaches the reaction and light from the reaction reaches the detector. In embodiments, a reaction support may be moved into or from the optical pathway through movement in any or all of the x, y, or z dimensions. In embodiments, a coagulation reaction support may be moved into communication with a light source and/or detector. In embodiments, the light source and/or the detector may be moved into communication with coagulation reaction support. In embodiments, one, two, or all three of the coagulation reaction support, light source, and detector may be movable relative to at least one of the other three. In embodiments, one or more fiber optic cables may be connected to a light detector such as a CCD sensor or PMT, in order to direct light from a location at least somewhat apart from the light detector to the light detector.

The reaction support/sample vessel can be back lit, front lit, or oblique (side) lit. Back lighting can be used for the purpose of detecting light scattering (nephelometry). The optical arrangement may take the form of a broad, evenly illuminated rear field, and a specifically shaped beam that is interrupted by the subject. Front-lit illumination may also be used.

In some embodiments, the optical set up for imaging coagulation is configured to measure scattered light. In one aspect, a set up for measuring scattered light includes a light source and a detector. The light source may provide diffuse light. The sample is held inside of a vessel such as an optically clear tip or other support. The vessel may be made of a clear material such as polystyrene or acrylic. The light path of the vessel (inner diameter) may be, for example, about 0.05, 0.1, 0.25, 0.5, 0.75, 1, 2, 3, 4, 5, 6, 7, 8, 9, 10, 15, 20, 25, or more millimeters. The vessel is placed in front of a detector, typically at a spacing of about 20-50 millimeters from the detector (although other spacing may be used). The detector can be any detector described elsewhere herein.

The detector may or may not include optical components such as lenses and filters. Filters may be used to reduce background by eliminating any stray light from the surroundings. The sample may be illuminated at right angles with respect to the detector (or any other non-zero angle to the illuminating beam). The light source may be oriented from the side (at approximately 90 degrees from the detector), from the top, or other position relative to the sample support. The light source can be any light source, diffuse or non-diffuse, and be of any wavelength, or a combination of wavelengths. The wavelength of the light source can be chosen to match the maximum spectral sensitivity of the detector.

In fluorescence excitation, subjects can be illuminated from the front for the purpose of fluorescence illumination. The light sources may be a single color light, such as an LED or laser. Oblique lighting can also be used in fluorescence excitation. The subjects are often excited at an angle, usually 90 degrees, from which the emitted photons will appear. This form of lighting enables scatter detection directly behind the subject (back lit) as well as the fluorescence emissions exiting from the side.

In some embodiments, fluorescent emission is imaged at 90 degrees to the excitation beam. In some embodiments, a photon source, typically a high-intensity LED, passes through a beam diffuser and a shaping lens, producing a collimated or gradually diverging excitation beam. The excitation beam passes through a band-pass filter and illuminates the sample, consisting of a vessel (tube, cuvette, or pipette tip) containing a solution with a fluorescently-labeled sample. Isotropically-emitted fluorescence is spectrally separated from excitation light with a long- or band-pass filter appropriate to pass Stokes-shifted fluorescence. Light is then imaged through a lens onto a digital camera or other detector. Fluorescence intensity is extracted from the resulting images via image analysis.

In other embodiments, transmitted light is imaged after optical filtering to remove the light at the exciting wavelength. In some embodiments, a photon source, typically a high-intensity LED, passes through a beam diffuser and a shaping lens, producing slowly divergent, elliptical excitation beam. The excitation beam passes through a band-pass filter and illuminates the samples, presented as one or more sample vessels (tube, cuvette, or pipette tip), each containing a solution with a fluorescently-labeled material. Isotropically-emitted fluorescence is spectrally separated from excitation light with a long- or band-pass filter appropriate to pass Stokes-shifted fluorescence. Light is then imaged through a camera lens onto a digital camera. Fluorescence intensity is extracted from the resulting images via image analysis. The optical setup can be used to produces array images of multiple tubes simultaneously.

In some embodiments, imaging may occur using fluorescence, darkfield illumination, or brightfield illumination.

Darkfield illumination may be achieved, for example, by the use of a ringlight (located either above or below the sample), a darkfield Abbe condenser, a darkfield condenser with a toroidal mirror, an epi-darkfield condenser built within a sleeve around the objective lens, or a combination of ringlight with a stage condenser equipped with a dark stop. Fundamentally, these optical components create a light cone of numerical aperture (NA) greater than the NA of the objective being used. The choice of the illumination scheme depends upon a number of considerations such as magnification required, mechanical design considerations, size of the imaging sensor etc. A ringlight based illumination scheme generally provides uniform darkfield illumination over a wider area while at the same time providing sufficient flexibility in mechanical design of the overall system.

Brightfield illumination may be achieved by the use of a white light source along with a stage-condenser to create Koehler illumination.

In some embodiments, an automatic filter wheel may be employed. The automatic filter wheel allows control of the imaging optical path to enable imaging of multiple fluorophores on the same field of view.

In some embodiments, image based auto-focusing may take place. An image-based algorithm may be used to control the z-position (e.g., vertical position) of an objective (i.e., its distance from the sample) to achieve auto-focusing. Briefly, a small image (for example, 128×128 pixels) is captured at a fast rate, for example using darkfield, brightfield, or other type of illumination. This image may be analyzed to derive the auto-focus function which is measure of image sharpness. Based on a fast search algorithm the next z-location of the objective is calculated. The objective may be moved to the new z-location and another small image may be captured. This closed-loop system does not require the use of any other hardware for focusing. The microscope stage may be connected to computer-controlled stepper motors to allow translation in the X and Y directions (e.g., horizontal directions). At every location, the desired number of images is captured and the stage is moved to the next XY position.

A camera with a CCD, EMCCD, CMOS or in some cases a photo-multiplier tube can be used to detect the signal.

Light Scattering Method

In some embodiments, the coagulation time can be determined by light scattering. The reaction mixture can be drawn into a pipette tip or capillary tube by either capillary force or by aspiration. The tip or capillary can be made of any optically clear material including but not limited to glass or a clear plastic such as polystyrene or polymethylmethacrylate (acrylic). In some embodiments, the pipette tip or capillary is long and thin. For example, if 1 µL of reaction mixture is drawn into a capillary of 0.5 mm diameter, a liquid column of about 5.1 mm results.

The pipette tip or capillary can then be sealed or capped, optionally to prevent sample evaporation during the assay. One suitable method for sealing the tip or capillary is to further aspirate a small volume of mineral oil. The pipette tip or capillary can also be coated in oil to improve imaging by reducing light scatter from the surface of the tip or capillary.

The pipette tip or capillary can then be suspended in front of a dark background and illuminated. In general, the direction of illumination is such that the light illuminates the tip or capillary but does not directly enter the camera or other photometric detector. For example, if the camera is in front of the tip or capillary, the light may enter from the side.

The tip or capillary is optically monitored. A simple photometric detector such as a photodiode or PMT can be used. A camera can also be used, optionally a video camera. Cameras may contain, for example, CCD or CMOS sensors. Use of a camera may be advantageous in some embodiments in that it allows one to determine the position of the sample by image processing, thereby making the method less sensitive to pipetting errors and sample placement. In some embodiments, the tip or capillary is monitored by reflectance or absorption spectroscopy.

When coagulation occurs, the fibrinogen polymerizes and increases the turbidity of the sample. Additional light is scattered from the reaction mixture, which is registered by the camera or photometric detector as an increase in the amount of illumination light scattered into the detector. FIG. 1 shows the reaction mixture before 100 and after 105 coagulation. Note the increase in turbidity from indicated positions 100 to 105. Also, in FIG. 1, the lower parts of the tips 101 are coated with oil, whereas the upper parts of the tips are not coated with oil 102. Note the lower amount of light scattering from the oil-coated part 101 of the tip as compared to the non-oil-coated part 102.

Image analysis allows one to analyze only the light which passes through the assay mixture, which is especially relevant to very small assay volumes. For example, using image analysis, light reflected or scattered from the walls of a vessel may be excluded from analysis. In another example, using image analysis, the size of the region of an image containing the assay mixture may be determined, which, in turn, may be used to determine the volume of the assay mixture in the vessel. This may, for example, permit the normalization of signals across different volumes of assay mixture. In another embodiment, by using image analysis, the position of a vessel containing the assay mixture or the position of an assay mixture in a vessel may be determined. This may permit accurate measurement of light from an assay mixture, even if the position of a vessel containing the assay mixture or the position of the assay mixture in a vessel may sometimes vary across different assay runs in the same optical set-up. In general, image analysis may permit the identification of regions of interest (ROI) in images for analysis. Typically, a ROI of an image is a portion of the total image which contains an image of the assay mixture. Optionally, a ROI may be identified in an image, and the intensity of light/signal in the ROI determined. For a given assay mixture of which multiple images are obtained, the intensity of signal in an ROI across multiple images of the same assay mixture may be measured and analyzed, and used to determine the time of coagulation in the assay mixture. Typically, a change in the coagulation status of the assay mixture results in a change in the signal in the ROI.

The time of onset of the increase in light scattering is the coagulation time for the diluted sample and may be appropriately transformed to give the appropriate coagulation parameter. Transformation of the diluted coagulation time to the coagulation parameter may be done through calibration of the system with independently characterized samples.

Analysis of Light Scattering Data

In embodiments where scattered light is measured as described above, data of the type shown in FIG. 2 may be obtained. As depicted, the mean signal is plotted against time. In this case time is on the horizontal axis and extends from just less than 50 seconds to just greater than 300 seconds on the right. Mean signal intensity is plotted on the vertical axis and extends from just less than 0.2 mean intensity units at the beginning of the reaction to just more than 0.45 units at the end. FIG. 3 shows the data from FIG. 2 fit to a four-parameter log-logistic function progress curve.

Figure 2:
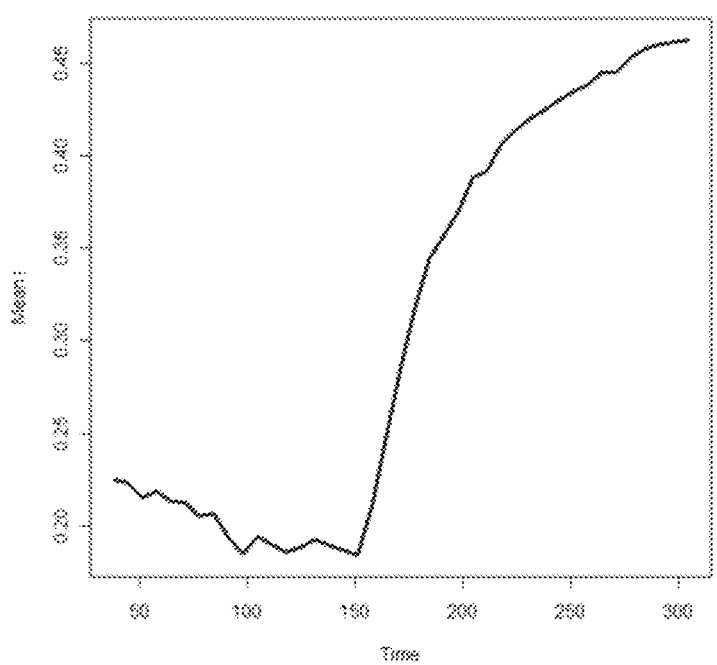
FIG. 2 shows a plot of mean light scattering signal versus time during coagulation of a plasma sample.
Figure 3:
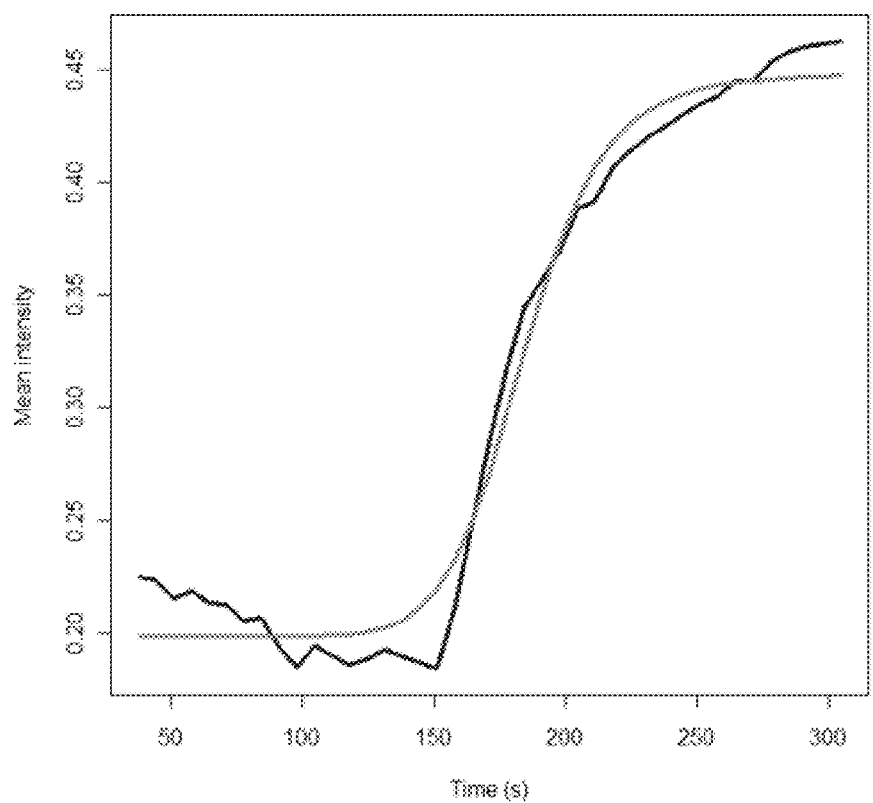
FIG. 3 shows a plot of mean light scattering signal versus time fit to a four-parameter log-logistic function progress curve.

In some embodiments, the coagulation time can be estimated from any defined part of the plotted data in FIG. 2 and/or the progress curve as depicted in FIG. 3. For example, the coagulation time can be defined to be where the light scattering reaches about 10%, about 50%, or about 80%, and the like of the maximum light scattering. The optimum point of the curve to use could be determined by correlation of the results with those of other accepted predicate methods for clinical samples with coagulation parameter values spanning the range of clinical concern.

Figure 19:
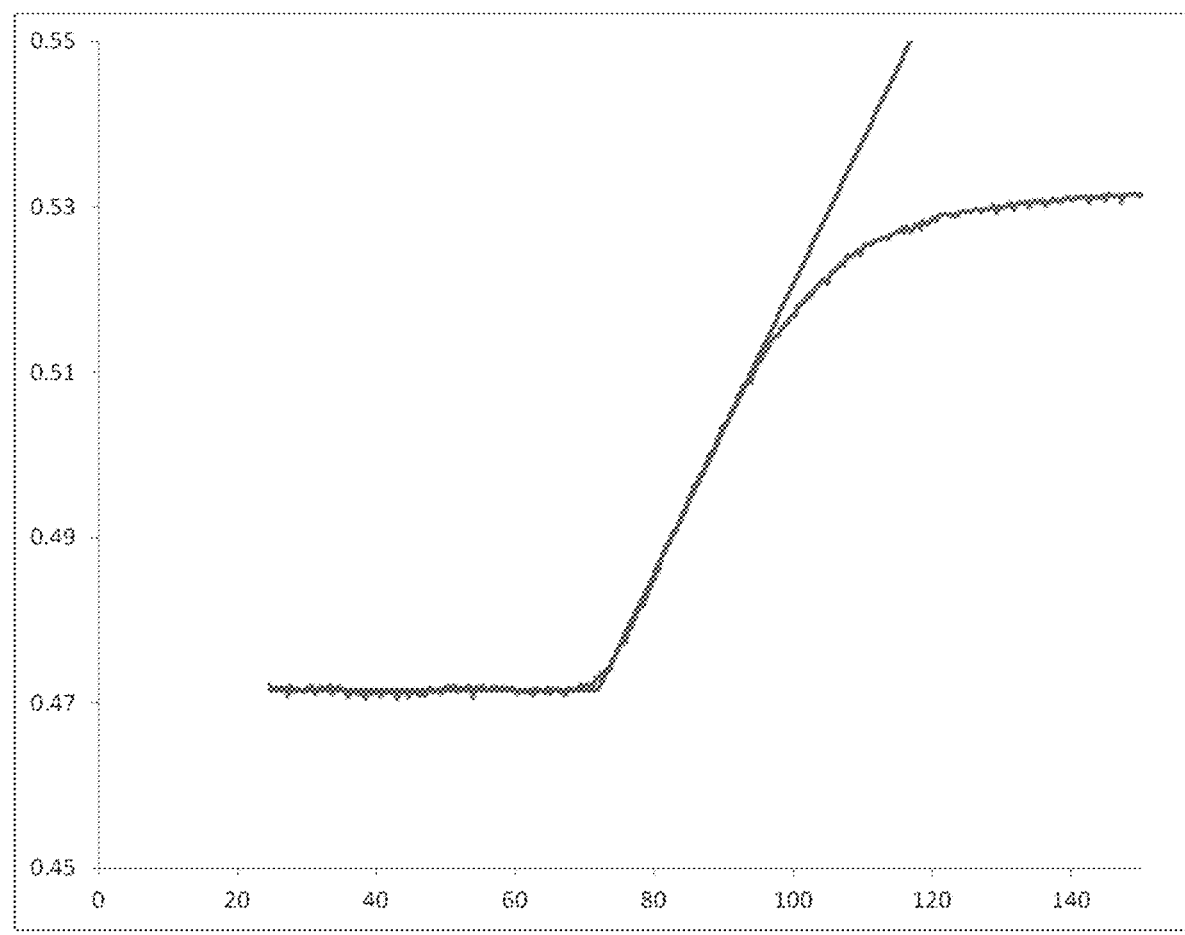
FIG. 19 shows a plot of mean light scattering signal versus time of a coagulation assay, fit to a bilinear curve.

In some embodiments, the scatter light intensity data may be fit to a curve as shown in FIG. 19. As depicted, the mean signal is plotted against time. In this case, time is on the horizontal axis and mean signal intensity is plotted on the vertical axis. In FIG. 19, the sigmoid curve is the mean light intensity data, and it is fit to the bilinear curve. In some embodiments, the coagulation time can be estimated from any defined part of the bilinear fit as depicted in FIG. 19. For example, the coagulation time can be defined where the light scattering signal reaches at least 10%, 20%, 30%, 40%, 50%, 60%, 70%, 80%, or 90% above the baseline level of light scattering.

In embodiments, methods involving analysis of light scattering by coagulation reactions may measure the quantity of light transmitted through a coagulation reaction. As a sample coagulates, it may become more opaque, scatter more light, and transmit less light. In embodiments, the coagulation time of assays in which light transmitted through a coagulation reaction is measured can be defined as the point where the amount of light transmitted through the coagulation reaction assay is decreased by at least 10%, 20%, 30%, 40%, 50%, 60%, 70%, 80% or 90% below the baseline level of light transmission through the sample.

Particle Bead Settling Method

In some embodiments, the coagulation time can be determined by the cessation or slowing of the rate of settling of microscopic particles or beads in the sample upon clot formation. Beads may be added to the sample at any suitable concentration at any time prior to coagulation. In some embodiments, the beads are a part of a concentrated or dried mixture of reagents that are mixed, suspended, and/or dissolved and re-suspended in the sample.

Figure 5:
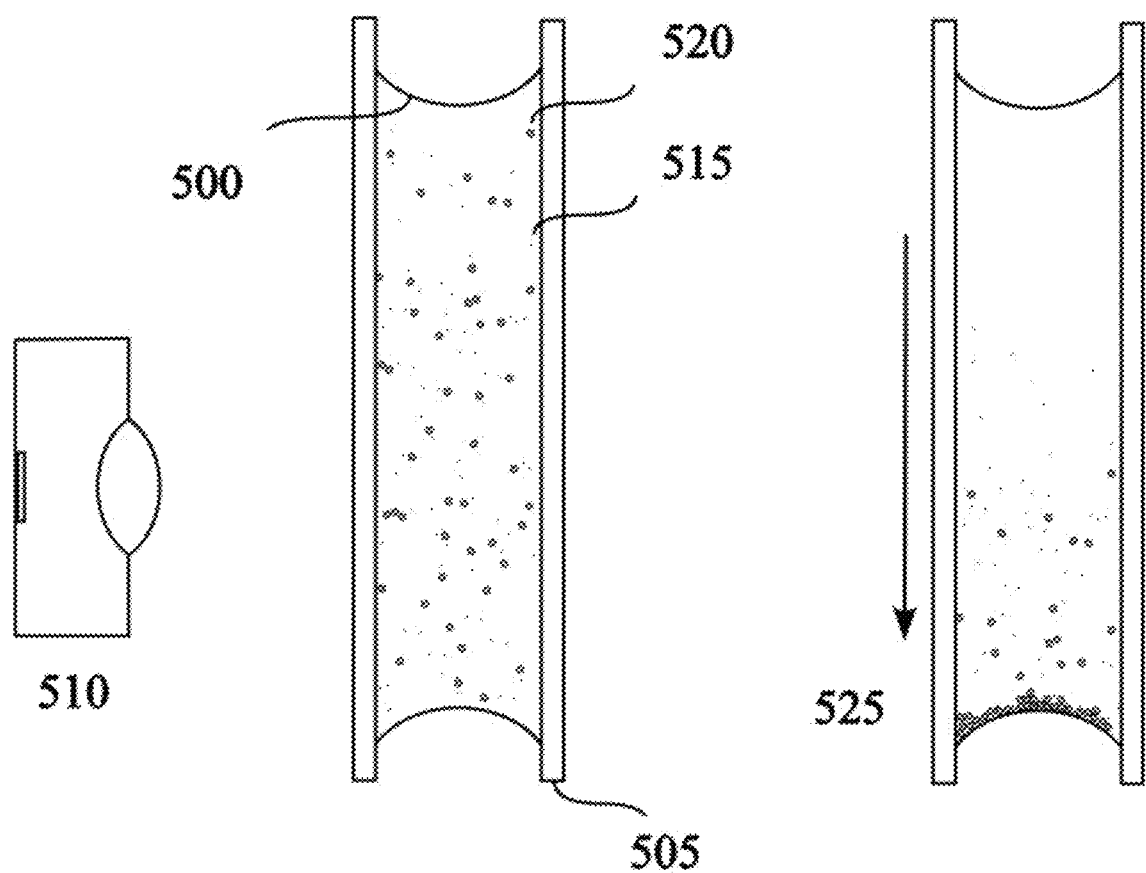
FIG. 5 shows a schematic of a bead settling embodiment.

Turning to FIG. 5, the method involves drawing the sample comprising beads 500 into a transparent vessel such as a capillary or pipette tip 505. The capillary or pipette type may have a narrow diameter, optionally about 0.5 mm. The capillary is typically oriented in the vertical such that the beads settle by force of gravity along the longest dimension of the tip or capillary. The settling of the beads is imaged over time by a camera 510. The camera may be a video camera and/or be coupled with a microscope capable of imaging the particles. In some embodiments, the visualization method is video microscopy. In some embodiments, the camera is a webcam. In some embodiments, the webcam is mounted about 10 mm from the capillary or tip.

The terms "beads" and "particles" are used interchangeably. The beads may have any size such that they settle at a suitable rate, which is slowed or ceases upon coagulation. In some embodiments, the beads have a diameter of about 5 µm, about 10 µm, about 20 µm, about 25 µm, about 30 µm, about 35 µm, about 40 µm, about 45 µm, about 50 µm, about 60 µm, or about 100 µm. In some embodiments, the beads have a diameter of at most about 5 µm, at most about 10 µm, at most about 20 µm, at most about 25 µm, at most about 30 µm, at most about 35 µm, at most about 40 µm, at most about 45 µm, at most about 50 µm, at most about 60 µm, or at most about 100 µm. In some embodiments, the beads have a diameter of between about 5 µm and about 100 µm, between about 20 µm and about 60 µm, or between about 25 µm and about 40 µm. The beads may be made of any suitable material including polystyrene or latex, they may be of any shape including spherical, and they may have any suitable density.

Beads of various sizes, of various shapes, having various densities, made of various materials, and the like may settle at different rates and/or be retained in a clot to various extents. In some embodiments, a mixture of beads having a distribution of sizes may be used. In some embodiments, a mixture of beads having a plurality of different sizes may be used. As shown in FIG. 5, a mixture of beads having a diameter of 25 µm 515 and beads having a diameter of 45 µm 520 may be used. A mixture of beads having various shapes, having various densities, made of various materials, and the like may also be used. In one aspect, mixtures of beads may be used. A mixture of beads may provide for a plurality of settling times and/or clot retention properties in order to improve the sensitivity of the method, reproducibility of the method, the range of clotting time measurable by the method, and the like.

As time progresses, the beads will settle under force of gravity as shown in FIG. 5, indication 525. In some embodiments, the bead motion may be driven by any other suitable force such as convection, air flow, magnetic fields, Brownian motion, and the like, optionally in combination with gravity. The beads could also float in the medium under gravity, if they have a density less than the medium. Without being held to any particular theory, even weak clots in diluted plasma are generally sufficient to overcome these weak forces such as gravity and prevent bead motion. In some embodiments, the strength of the clots can be increased by addition of exogenous fibrinogen as described above. In some embodiments, the bead settling method may use less exogenous fibrinogen than the light scattering method. The clotting time may be the time at which the beads cease to move under the weak force and/or the time at which the rate of movement under the weak force decreases substantially.

In some embodiments, the clotting time may be determined by analyzing the images to determine when bead motion ceases. In some embodiments, the image analysis may be automated, optionally by any suitable algorithm. For example, a difference parameter such as the mean squared difference between each pixel of each frame and the final frame of the video may be calculated. When clotting occurs and bead motion ceases, the final frame of the video will approximately resemble all frames between clotting and the end of the video. In this example, the difference parameter will drop to near zero as soon as clotting has occurred. The time that this drop begins represents the clotting time, which can be transformed into a coagulation parameter as appropriate.

In another embodiment, the peak signal-to-noise ratio ("PSNR") can be used to determine the coagulation time. PSNR assesses the difference between images "I" and "K" by the mean squared error ("MSE") as defined in Equation 2

$$MSE = \frac{1}{mn}\sum_{i=0}^{m-1}\sum_{j=0}^{n-1}[I(i,j) - K(i,j)]^2 \quad \text{(Equation 2)}$$

wherein PSNR is defined in Equation 3

$$PSNR = 10 \cdot \log_{10}\left(\frac{MAX_I^2}{MSE}\right) \quad \text{(Equation 3)}$$
$$= 20 \cdot \log_{10}\left(\frac{MAX_I}{\sqrt{MSE}}\right)$$

with MAXI being the maximum intensity of the image, and "m" and "n" being the image dimensions in pixels (width by length).

Figure 4:
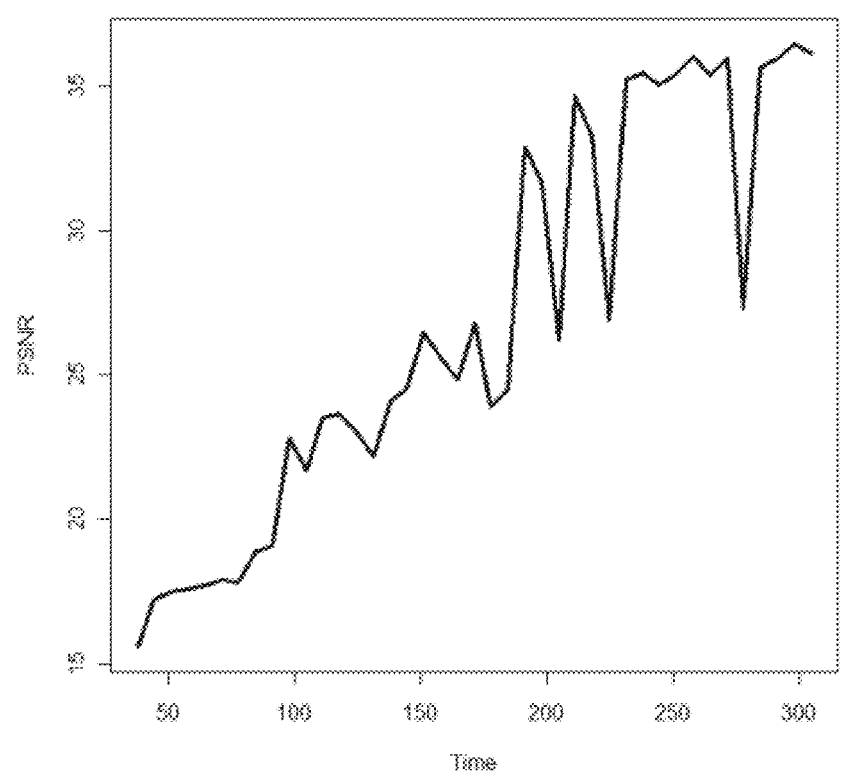
FIG. 4 shows a representative reaction time course analyzed by the PSNR method.

FIG. 4 shows a representative reaction time course analyzed by the PSNR method. The PSNR progress curve is shown with the PSNR value along the vertical scale extending from 15 to just above 35 at the top. The time is shown on the horizontal axis extending from just below 50 to just above 300 seconds on the right. In some embodiments, the PSNR data are fit with a simple function such as a linear or quadratic function and the mid-point of the increase can be determined and related to a coagulation parameter though calibration as described.

In some embodiments, the coagulation time can be determined by microscopy. In one embodiment, the coagulation of whole blood can be measured by observing the movement of red blood cells under microscopy. The whole blood sample may be diluted. In assays containing red blood cells, the red blood cells perform a similar function as the beads described in the bead settling method above.

Fluorescent Microscopy Method

In some embodiments, the coagulation time can be determined by observing the movement of fluorescent beads by fluorescent microscopy. Suitable fluorescent beads include carboxylate-modified microspheres. Suitable carboxylate-modified microspheres may be obtained from Life Technologies Inc., Carlsbad Calif., under the trade name Fluo-Spheres, catalog #F-8816. The fluorescent beads can fluoresce at any suitable wavelength, including in the crimson part of the spectrum. The fluorescent beads may also be any suitable size. In some embodiments, the beads have a size such that they do not settle by gravity or settle slowly by gravity in the reaction medium, and that they cease to move when the sample coagulates. In one embodiment, the fluorescent spheres have a diameter of about 1 µm.

Figure 6:
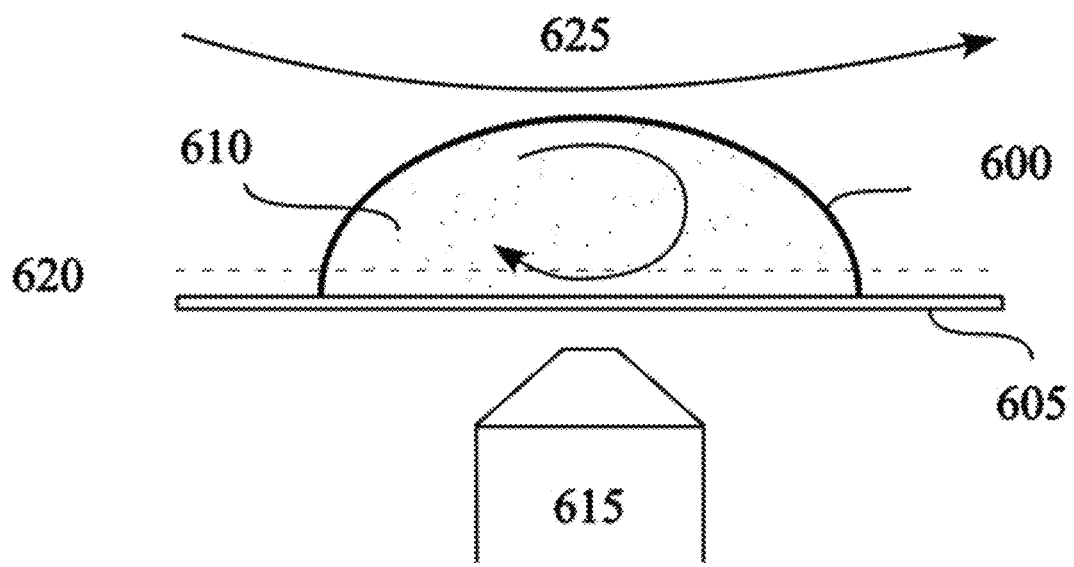
FIG. 6 shows a schematic of a fluorescent microscopy embodiment.

As in the bead settling method described above, the fluorescent beads may be at any suitable concentration, added along with other dried reagents, and the like. As shown in FIG. 6, the sample 600 is not necessarily drawn into a capillary or pipette tip and may be placed as a drop on a slide 605. The sample comprising fluorescent beads 610 may be of any suitable volume, including about 2 µL. The microscope objective piece 615 images the sample at a focal plane 620. The position of the slide 605 relative to the microscope objective piece 615 can be varied to change the depth of the focal plane 620 and/or image various areas of the sample. In some embodiments, the slide can be systematically moved relative to the microscope objective piece so that several fields of view within the assay reaction volume are captured. The relative position of the slide and the microscope objective piece can also insure that only the sample is visualized and not background areas.

Figure 7:
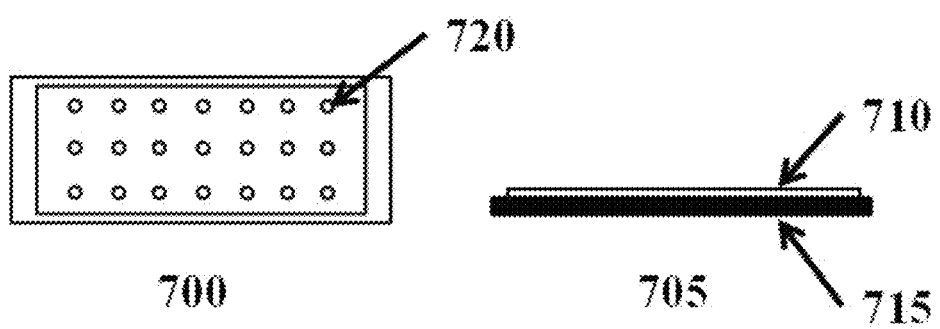
FIG. 7 shows a schematic of a cuvette suitable for microscopy embodiments.

In some embodiments, the sample is placed on a cuvette. The cuvette may be imaged by positioning it in relation to the microscope objective 615, or the cuvette may be placed on a slide 605. An exemplary cuvette is depicted in FIG. 7 in a top view 700 and a side view 705. The exemplary cuvette has two layers. A top layer 710 may be an acrylic spacer material and the bottom layer 715 can be a standard glass cover-slip. The top layer may have any suitable thickness, including approximately 80 μm. The top layer may also have ports 720, optionally about 2 mm in diameter, optionally created with a laser cutter. The acrylic material comprising the top layer 710 may have an adhesive side which sticks to the bottom layer 715. The top layer and bottom layer are assembled such that miniature sample wells 720 of about 2 mm diameter and 80 μm depth are created, which are capable of holding about 0.25 μL of sample.

In some embodiments, the cuvette is made from thin slabs of light-transmissive acrylic with machined ports for sample holding. In some embodiments, the cuvette is made of injection molded plastic with a plasma-etched surface to render the cuvette hydrophilic.

The movement of the fluorescent beads is driven by a mixture of air flow (FIG. 6, indication 625), convection and Brownian motion. In some embodiments, the sample is illuminated at the excitation wavelength of the fluorescent beads. In some embodiments, the sample is illuminated with a xenon arc lamp. The fluorescent beads emit radiation at an emission wavelength, which may be observed by a microscope. In some embodiments, the microscope may be an inverted fluorescence microscope where the microscope objective 615 is below the sample 600. The microscope may have any suitable power of magnification such that the fluorescent beads are imaged and their motion can be analyzed. In one embodiment, a 20× objective lens is used. The motion of the beads is recorded by a camera. The camera may be a cooled CCD camera. The images may be taken at any suitable rate, including at a rate of about 5 frames per second. In some embodiments, the images are acquired at the emission wavelength of the fluorescent beads.

The clotting time may be determined by analyzing the recorded images to determine when motion of the fluorescent beads ceases. In some embodiments, 100 to 200 images are acquired. The images can be analyzed as described herein to determine coagulation time, which is related by calibration to a coagulation parameter as described herein.

In one embodiment, the coagulation of whole blood can be measured by observing the movement of red blood cells under microscopy. The whole blood sample may be diluted. In some embodiments, the red blood cells may be fluorescently labeled. The red blood cells may be observed by regular microscopy, or, in the event they are fluorescently labeled, by fluorescent microscopy. In assays containing red blood cells, the red blood cells perform a similar function as the beads described in the fluorescent microscopy method above.

Propelled Liquid Column Method

In some embodiments, the coagulation time can be determined by imaging of the bulk movement of a sample. In this method, the coagulated sample adheres to the interior of a vessel such as the inside of a capillary and ceases to move following coagulation. The sample can be moved by any method including pneumatic means.

The movement can be in any manner including reciprocating, circular, and the like. The movement can be regular or irregular and traverse any suitable distance. In some embodiments, the bulk movement is on the order of several millimeters, such as about 1 mm, about 2 mm, about 4 mm, about 6 mm, about 8 mm, about 10 mm, about 20 mm, or about 30 mm. In some embodiments, the bulk movement is at least about 1 mm, at least about 2 mm, at least about 4 mm, at least about 6 mm, at least about 8 mm, at least about 10 mm, at least about 20 mm, or at least about 30 mm. In some embodiments, the bulk movement is at most about 1 mm, at most about 2 mm, at most about 4 mm, at most about 6 mm, at most about 8 mm, at most about 10 mm, at most about 20 mm, or at most about 30 mm.

The movement can have any suitable frequency or occur on any suitable time scale. In some embodiments, the bulk movement is on the order of seconds such as about 0.5 s, about 1 s, about 2 s, about 4 s, about 6 s, about 8 s, or about 10 s. In some embodiments, the bulk movement is on a time scale of at most about 0.5 s, at most about 1 s, at most about 2 s, at most about 4 s, at most about 6 s, at most about 8 s, or at most about 10 s.

The sample may be blood or plasma. In the propelled liquid column methods, microscopic imaging may not be necessary. The relevant image is generally the position of the bulk fluid sample in relation to the capillary vessel. The vessel is generally transparent so, in the case of blood, the sample will be easily distinguished by its red color. Plasma is generally essentially transparent, so detection of a bulk plasma sample may be more difficult in some embodiments. In some embodiments, plasma samples can be imaged due to refraction of light from the liquid-air meniscus at the end of the sample in the capillary tube. If the menisci are difficult to locate by imagery in a particular embodiment, a dye or other suitable material may be added to the sample to improve visualization of the menisci. In another example, even if not initially visible, the menisci may become visible due to light scattering once coagulation has occurred.

The sample can be diluted or not diluted. Some examples, potentially including embodiments utilizing diluted plasma, may not form a suitably strong clot in some cases. However, the clot can be made suitably strong by reinforcing it with addition of exogenous fibrinogen or a high volume fraction of neutrally buoyant beads. Without being bound by theory, the beads provide a greater surface area for the incipient clot to bind to, which stiffens or increases the effect of increasing viscosity of the reagent and sample mixture and allows the clot formed to adhere to the capillary and stop moving. The volume fraction can be any suitable fraction such that the clot adheres to the capillary. In some embodiments, an assay is prepared such that about 20%, about 30%, about 40%, about 50%, about 60%, about 70%, about 80%, or about 90% of the assay volume is beads. In some embodiments, an assay is prepared such that at least about 20%, at least about 30%, at least about 40%, at least about 50%, at least about 60%, at least about 70%, at least about 80%, or at least about 90% of the assay volume is beads. The beads can be larger in the propelled liquid column methods, for example about 10 μm in diameter. The addition of beads may have another advantageous effect in that they increase the effective sample volume and thus may aid in visualization of small sample volumes without contributing to dilution of the sample.

Image Processing and Analysis

Images may be acquired by the small volume coagulation measurement methods described herein. In general, the images are acquired over a period of time, generally longer than the coagulation time. The last image captured is generally an image of the coagulated sample.

The pixilation of images, including exemplary numbers of pixels is described above. In some embodiments, each image comprises an array of 512 by 512 pixels (262,144 total pixels). Each image may be divided into 16 strips of dimension 512 by 32 (row by column, or column by row). Each strip may then be converted into its respective Fourier-transformed image and re-assembled to form a modified 512 by 512 image with Fourier-transformed strips. In some embodiments, a reference image is created by taking the last image acquired and transforming it in the same manner.

In some embodiments, such as analysis of the particle bead settling method and the fluorescence microscopy method (described above), the analysis involves calculating the correlation coefficients of each column of a transformed image with the corresponding column of the transformed reference image. The correlation coefficient may be calculated according to Equation 4, $$\rho = \frac{\sum_{i=1}^{n}(x_i - \overline{x_i})\left(x_i^{ref} - \overline{x_i^{ref}}\right)}{\sqrt{\sum_{i=1}^{n}(x_i - \overline{x_i})^2}\sqrt{\sum_{i=1}^{n}\left(x_i^{ref} - \overline{x_i^{ref}}\right)^2}}$$ (Equation 4)

where $x_i$ and $x_i^{ref}$ are the $i^{th}$ element of a column of an image and the reference image respectively. Values of the correlation factor vary from 0 to 1. The correlation factor for the final image (correlated to itself) would be 1.0.

A correlation factor may be obtained for each column, and the overall correlation of the two images is the median value of the correlation factor calculated over all columns. Thus, for every image, a single value quantifying its correlation with the reference image may be calculated.

Figure 8:
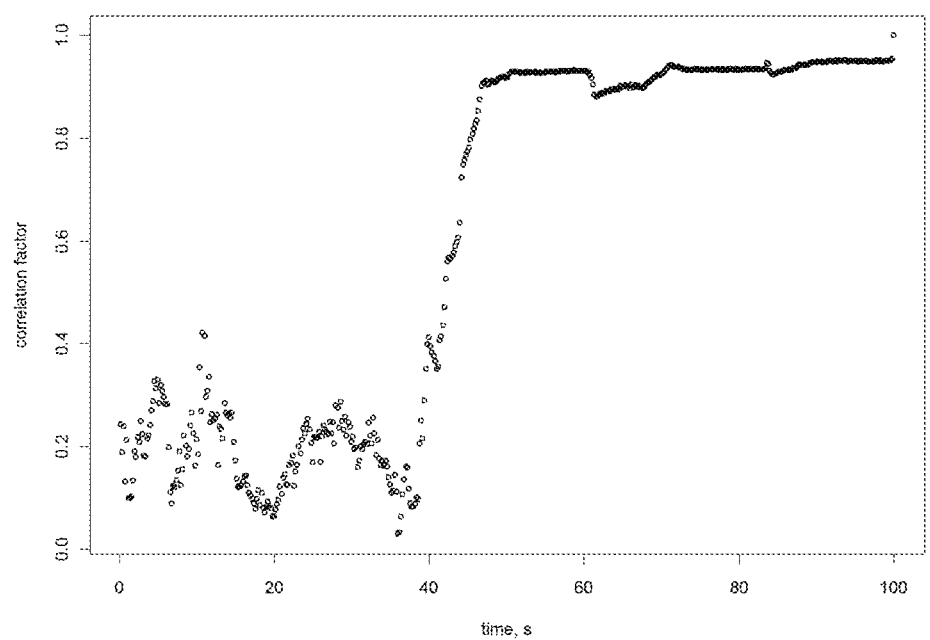
FIG. 8 shows a plot of correlation factor as a function of time for measurement of PT activation factor of a plasma sample.

In some embodiments, the correlation factors are plotted as a function of time as shown in FIG. 8. In this example for measurement of PT in a plasma sample, the correlation factor is on the vertical axis and ranges from 0.0 to 1.0 at the top. Time is on the horizontal axis and ranges from 0 to 100 seconds on the right. At times less than the coagulation time, the images are poorly correlated with the final image, potentially due to particle movement by both convective and Brownian diffusive forces. At the onset of coagulation, the fluid transitions into a gel and the particles become locked in place. As seen in FIG. 8, this phase transition is indicated by a dramatic rise in the calculated correlation factor, since beyond coagulation, the particle positions do not change significantly and are hence strongly correlated with the final image. In this example the coagulation time appears to be around 40 seconds. In an automated set-up a sigmoidal curve could be fitted to the data to estimate the inflection point indicative of coagulation time.

In some embodiments, coagulation times measured for diluted samples are longer than those obtained for other methods that do not use diluted samples. The results for diluted samples can be made to conform with results of non-diluted samples by correlating the results of the different methods and applying a mathematical correction designed to give results from diluted samples which are equivalent to results from a method for non-diluted samples.

Video Imaging Considerations

In some embodiments, video imagery is used to determine the coagulation time. For instance where the settling of particles or changes in light scattering are measured, one may need to image a significant fraction of the reaction volume while excluding substantially all background. This objective may be achieved by using feature recognition software.

Figure 9:
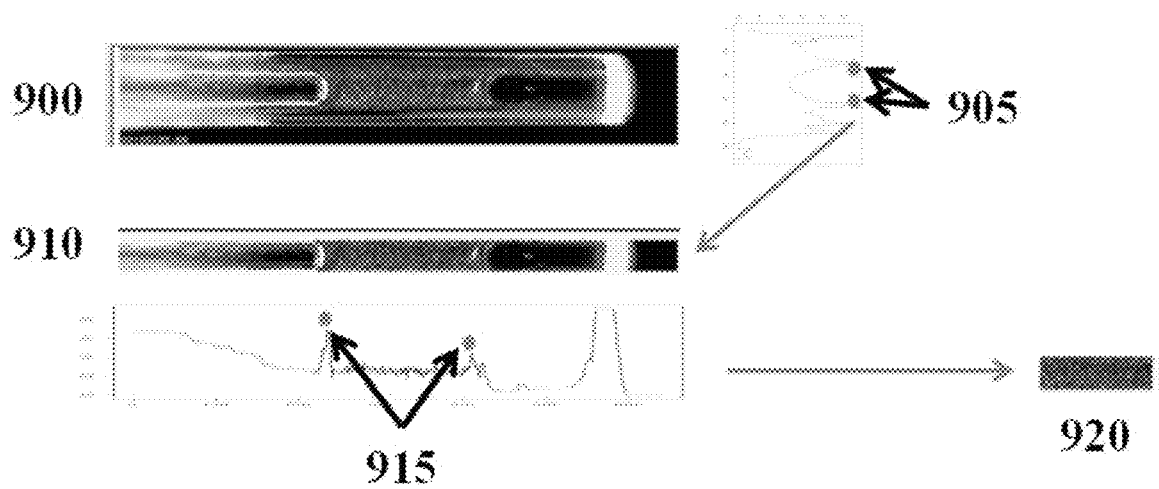
FIG. 9 shows a method for excluding background from video images.

Turning to FIG. 9, an image of the assay cuvette 900 is made. The walls of the cuvette are identified due to refractive index differences 905 and excluded from the image 910. The menisci of the reaction volume are also identified 915 and excluded from the image 920. The final cropped image 920 may then be used for image analysis. In embodiments, a cropped image may a region of interest (ROI) of the image. In embodiments, procedures provided herein for cropping images may also be used with still images.

Measurement of Clotting Factors

Methods, devices, and systems for measuring the concentration and/or activity of a clotting factor are also provided herein. Methods for measuring concentration and/or activity of a clotting factor may be performed in a multiplexed manner, or in a device or system capable of multiplexed analysis, optionally wherein multiple assays are performed with a single drop of blood. In some aspects, one or more clotting time assays are performed with blood sample from a subject, and one or more assays directed to the concentration and/or function of a clotting factor is also performed. In some aspects, if the coagulation time for a blood sample from a subject is outside of a certain range, a blood sample from the subject will also be analyzed for the concentration and/or function of a clotting factor. This procedure may be carried out in a system or device that is programmed to perform an assay for a clotting factor if a blood sample has a certain clotting time. The system or device may also be programmed remotely, such as by a cloud-computing infrastructure.

Certain coagulation parameters may be measurable by methods other than by a coagulation time. For example, described herein are methods, devices and systems for measuring the concentration and/or function of any of the clotting factors and/or regulators thereof. Exemplary clotting factors and/or regulators thereof include von Willebrand factor, Factor I (fibrinogen), Factor Ia (fibrin), Factor II (prothrombin), Factor IIa (thrombin), Factor V, Factor Va, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, collagen, platelets, platelet-activating factor, platelet factor 4, thromboxane $A_2$, protein kinase C, phospholipase $A_2$, tissue factor, high-molecular-weight kinninogen, prekallikrein, kallikrein, protein C, thrombomodulin, calcium, vitamin K, protein S, antithrombin, tissue factor pathway inhibitor (TFPI), plasmin, tissue plasminogen activator (t-PA), prostacyclin, and the like. In the clotting factor nomenclature, the lowercase "a" indicates the active form. For example Factor XIIa is the active form of Factor XII. In some embodiments, the methods described herein distinguish between active and inactive forms of clotting factors.

In some embodiments, the concentration and/or activity of a clotting factor may be measured by enzyme-linked immunosorbent assay (ELISA). Performing an ELISA involves at least one antibody with specificity for a particular antigen (e.g. a clotting factor). The sample with an unknown amount of antigen is immobilized on a solid support either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the immobilized materials are typically washed with a mild detergent solution to remove any proteins or antibodies that are not specifically bound. After the final wash step, the plate is developed by adding an enzymatic substrate to produce a visible signal, which indicates the quantity of antigen in the sample. Methods for performing ELISA reactions with small volumes are described in, for example, U.S. Pat. No. 8,088,593, which is herein incorporated by reference in its entirety for all purposes. As described therein, colorimetric methods such as ELISA may benefit from multi-color imaging and multiple light pathways when performed in small volumes.

Multi-Color Images and Multiple Light Pathways

One aspect described herein provides for coagulation analysis using image-based analysis. The system can include a camera that can measure an optical signal using one or more detection spectrum regions. For example, a camera can measure an optical signal using red, green, and blue detection spectrum regions. The measured signal can include three measured values that can be interpreted using one or more algorithms described herein. The use of more than one detection spectrum region can increase the dynamic range of an assay and can increase the accuracy of a measurement as compared to measurements using a single detection spectrum region.

Also provided herein are systems, devices, and methods for performing optical measurements on samples and assay reaction products that are contained within reaction chambers, each with a plurality of distinct path lengths. The reaction chambers can have a plurality of distinct path lengths such that a greater or lower amount of light absorbance is observed. The plurality of distinct path lengths allows for an increase in the dynamic range of a selected assay protocol. The image of the reaction chamber can be analyzed as described herein to obtain information on the sample or the assay reaction products. The combination of utilizing the plurality of available path lengths within a single reaction chamber and the use of three channel detection spectrum regions greatly enhances the dynamic range of a given assay.

Computer Implementation

The methods, devices and systems described herein may be implemented with aid of a programmable computer. For example, the image pixilation, the analysis of light scattering data, the image processing and analysis, video image processing methods, and the like may be programmed into a computer and/or performed by a programmed computer. Computer assistance may be preferred for achieving a rapid, automated method, device or system.

For example, a computer-assisted method for characterizing an analyte suspected to be present in a sample may be used. The computer-assisted method may comprise obtaining a digital image of the sample, wherein the digital image comprises at least a two-dimensional array of pixels, and wherein each pixel comprises a plurality of intensity values, each of which corresponds to a distinct detection spectral region; correlating, with the aid of a programmable device, the obtained intensity values with a predetermined set of values that define a dynamic range of each detection spectral region; and predicting the presence and/or quantity of the analyte in the sample based on the correlating of the obtained intensity values with a predetermined set of values.

Additional Assays

The methods, devices, and systems described herein may be used for analyzing any assay that results in the change in viscosity or solid/liquid state of a sample. For example, as described herein, beads may be added to any assay that results in the change in viscosity or solid/liquid state of a sample, and image analysis of the movement of the beads may be used to determine the time of change in viscosity or solid/liquid state of the sample. In other examples, as described herein, the change in turbidity of a sample may be monitored by light scattering. Any assay that results in the change in viscosity or solid/liquid state of a sample and/or a change in light scattering may be monitored by methods provided herein. In other examples, as described herein, the change in viscosity or solid/liquid state of a sample may be monitored by imaging the movement of the sample through a column. Assays that may be analyzed by the methods provided herein include assays that do not involve blood coagulation factors, as long as the assay results in the change in viscosity or solid/liquid state or light scattering of a sample. For example, in some embodiments, agglutination assays may be analyzed by methods provided herein. Other examples of assays that may be analyzed by methods provided herein include: (1) platelet aggregation assays, (2) nephelometric immunoassays, (3) particle-enhanced nephelometric immunoassays, (4) turbidometric immunoassays, (4) latex agglutination immunoassays, and (5) Limulus Amebocyte Lysate (LAL) test (for example, for detecting bacterial endotoxins and bacterial diseases).

EXAMPLES

Example 1

PT Measurement by Light Scattering

Measurement of the PT coagulation parameter by light scattering was performed with the following materials:
  Plasma samples: QuikCoag™ Control Level 1 (Normal Coagulation Plasma Control); QuikCoag™ Control Level 2 (Low Abnormal Coagulation Plasma Control); and QuikCoag™ Control Level 3 (High Abnormal Coagulation Plasma Control) (each from BioMedica Diagnostics Inc., Nova Scotia, Canada)
  Bovine fibrinogen (Sigma-Aldrich) 10 mg/ml stock in Hepes Buffered Saline (HBS) pH 7.4
  Reconstituted PT reagent (QuikCoag™ PT plus Calcium, BioMedica Diagnostics Inc., Nova Scotia, Canada)
  1× Hepes Buffered Saline (HBS)
  0.02 M $CaCl_2$ These materials were used in the following procedure to measure the PT coagulation parameter by light scattering. All steps were performed at room temperature, using an automated liquid handler.

Figure 10:
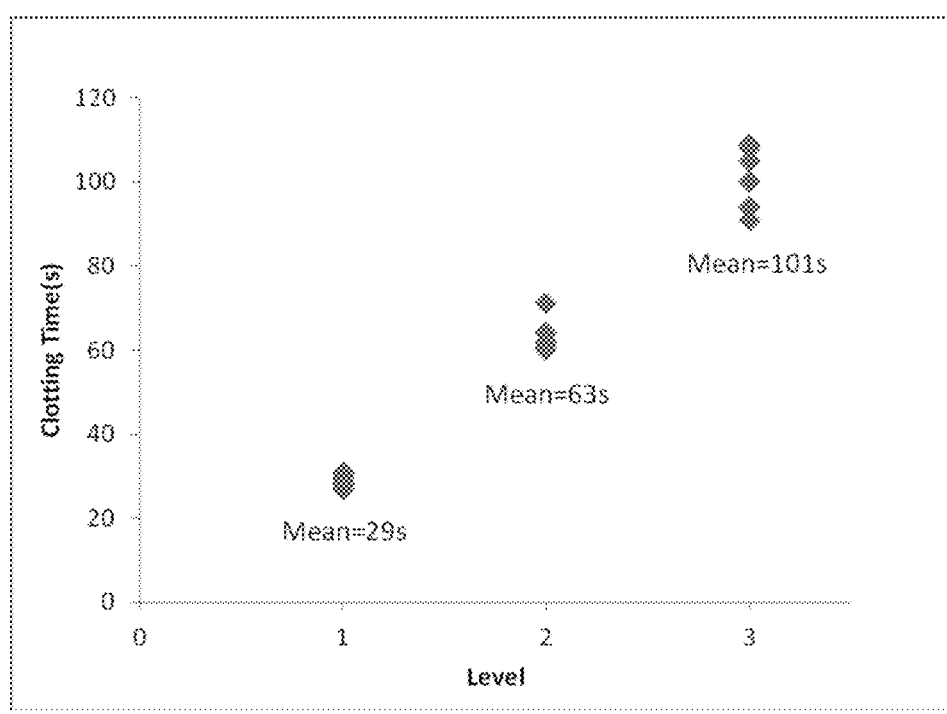
FIG. 10 shows exemplary results of measuring PT by light scattering.

1) Fibrinogen was dissolved 2.5 mg/ml in PBS (solution A)
2) Mixed 0.2 volumes of each plasma sample with 0.8 volumes solution A (i.e. each plasma sample was diluted 5-fold)
3) At t=0, mixed 1 volume of diluted plasma with 1 volume PT reagent and aspirated 2 µl of the mixture into a tip.
4) Aspirated 1 µl mineral oil, dipping tip deep enough in oil to cover viewing area
5) Moved to camera/photodetector and began video recording
6) Stopped recording after clotting occurs (typically <10 minutes)
7) Repeated steps 3-6 four additional times Exemplary results are shown in FIG. 10. Here, the clotting time is shown on the vertical axis and extends from 0 to 120 seconds. Levels 1, 2, and 3 on the horizontal axis refer to QuikCoag™ Control Level 1, 2, and 3 samples, respectively. The five different points for each level show the separate result of replicate assays with each of the Level 1, 2, and 3 plasma samples. The mean value provided on the graph indicates the mean clotting time in seconds for the five assays performed with each of the Level 1, 2, and 3 plasma samples. The PT coagulation parameter was determined by light scattering. Briefly, to determine the coagulation parameter, images from the video recording were subjected to automated processing, in which regions of interest (ROI) containing only the reaction mixture were defined. The region of interest for each tip was defined as the region between the walls of the tip and between the menisci of the reaction mixture in the tip. The top meniscus is the air/reaction mixture interface, and the bottom meniscus is the reaction mixture/oil interface. After the definition of the region of interest, the analysis algorithm determined the average light intensity in the ROI for each frame of the video recording was determined. The coagulation time was defined as the time when the average light intensity in the ROI began to rise over the baseline level.

Example 2 aPTT Measurement by Light Scattering

Figure 11:
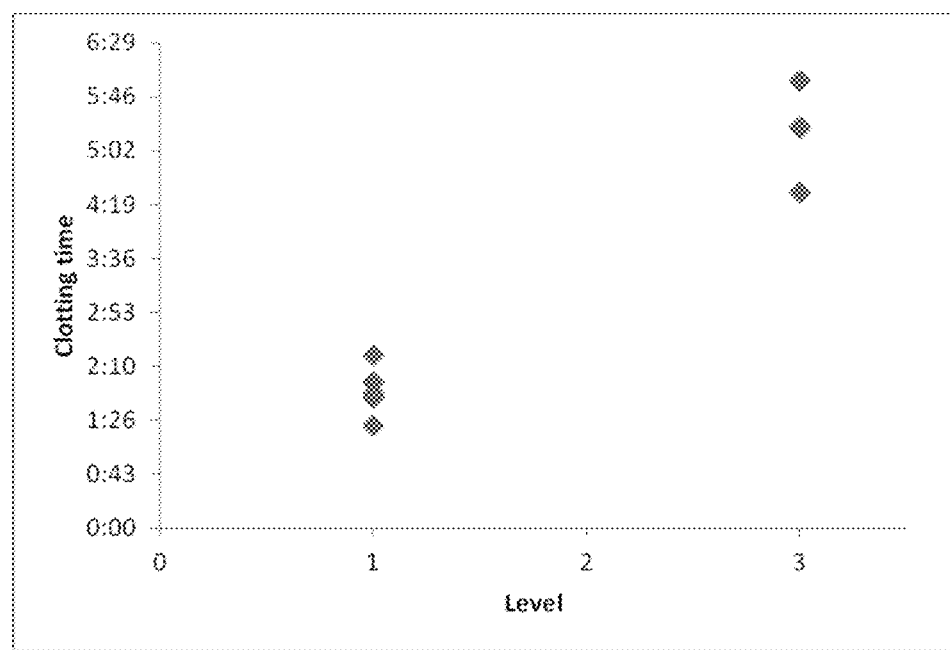
FIG. 11 shows exemplary results of measuring aPTT by light scattering.

Measurement of the aPTT coagulation parameter by light scattering was performed with the following materials:
  QuikCoag™ Control Level 1 (Normal Coagulation Plasma Control) and QuikCoag™ Control Level 3 (High Abnormal Coagulation Plasma Control) (each from BioMedica Diagnostics Inc., Nova Scotia, Canada)
  Bovine fibrinogen (Sigma-Aldrich) 10 mg/ml stock in Hepes Buffered Saline (HBS) pH 7.4
  Reconstituted aPTT reagent (QuikCoag™ APTT, BioMedica Diagnostics Inc., Nova Scotia, Canada)
  1× Hepes Buffered Saline (HBS)
  0.02 M $CaCl_2$ These materials were used in the following procedure to measure the aPTT coagulation parameter by light scattering. All steps were performed at room temperature, using an automated liquid handler.
  1) Fibrinogen was dissolved 5 mg/ml in PBS (solution A)
  2) Mixed 0.2 volumes of each plasma sample with 0.8 volumes solution A (i.e. each plasma sample was diluted 5-fold)
  3) Mixed 1 volume of diluted plasma with 1 volume of aPTT reagent and incubated for 3 minutes
  4) At t=0, mixed 1 µl of the mixture with 1 µl of 0.2M $CaCl_2$ and aspirated into tip.
  5) Aspirated 1 µl mineral oil, dipping tip deep enough in oil to cover viewing area
  6) Moved to camera/photodetector and began video recording
  7) Stopped recording after clotting occurred (typically <10 minutes)
  8) Repeated steps 3-7 two (Level 3 sample) or four (Level 1 sample) more times Exemplary results are shown in FIG. 11. Here, the clotting time is shown on the vertical axis and extends from 0 to 6:29. Levels 1 and 3 on the horizontal axis refer to QuikCoag™ Control Level 1 and 3 samples, respectively. The different points for each level show the separate result of replicate assays with each of the Level 1 and 3 plasma samples. The aPTT coagulation parameter was determined by light scattering as described in Example 1.

Example 3

PT Measurement by Bead Settling

Figure 12:
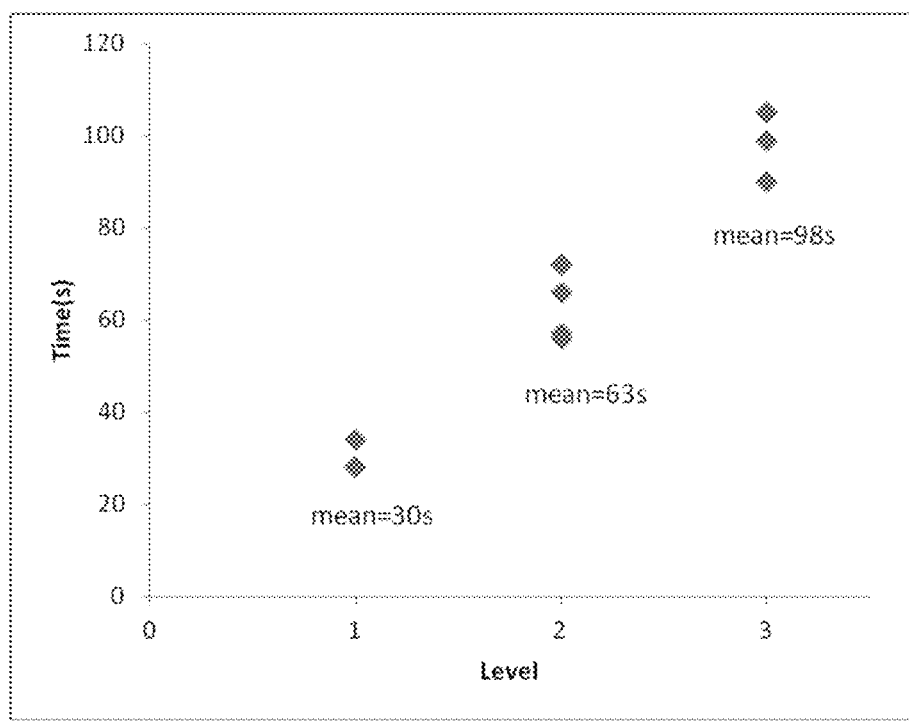
FIG. 12 shows exemplary results of measuring PT by bead settling.

Measurement of the PT coagulation parameter by bead settling was performed with the following materials:
  Plasma samples: QuikCoag™ Control Level 1 (Normal Coagulation Plasma Control); QuikCoag™ Control Level 2 (Low Abnormal Coagulation Plasma Control); and QuikCoag™ Control Level 3 (High Abnormal Coagulation Plasma Control) (each from BioMedica Diagnostics Inc., Nova Scotia, Canada)
  Reconstituted PT reagent (QuikCoag™ PT plus Calcium, BioMedica Diagnostics Inc., Nova Scotia, Canada)
  Bead slurry (e.g. 1:1 mixture of 25 um and 45 um diameter beads (e.g. Polybead Microspheres, Polysciences, PA), washed in HBS, centrifuged, and excess liquid removed)
  1× HBS (Hepes Buffered Saline pH7.4)
  0.02 M $CaCl_2$ These materials were used in the following procedure to measure the PT coagulation parameter by bead settling. All steps were performed at room temperature, using an automated liquid handler.
  1) Each plasma sample was diluted 5-fold with HBS
  2) Mixed beads 1:4 with PT reagent (e.g. 10 µl beads+40 µl PT reagent)
  3) At t=0, mixed 1 µl of diluted plasma with 1.25 µl of bead/PT reagent mixture and aspirated into tip
  4) Aspirated 1 µl mineral oil, dipping tip deep enough in oil to cover viewing area
  5) Moved to camera and begin video recording
  6) Stopped recording after clotting occurred (typically <10 minutes)
  7) Repeated steps 3-6 one (Level 1 sample), three (Level 2 sample), or two (Level 3 sample) more times Exemplary results are shown in FIG. 12. Here, the clotting time is shown on the vertical axis and extends from 0 to 120 seconds. Levels 1, 2, and 3 on the horizontal axis refer to QuikCoag™ Control Level 1, 2, and 3 samples, respectively. The different points for each level show the separate result of replicate assays with each of the Level 1, 2, and 3 plasma samples. The mean value provided on the graph indicates the mean clotting time in seconds for the assays performed with each of the Level 1, 2, and 3 plasma samples. The PT coagulation parameter was determined by the bead sedimentation assay, as described elsewhere herein.

Example 4 aPTT Measurement by Bead Settling

Figure 13:
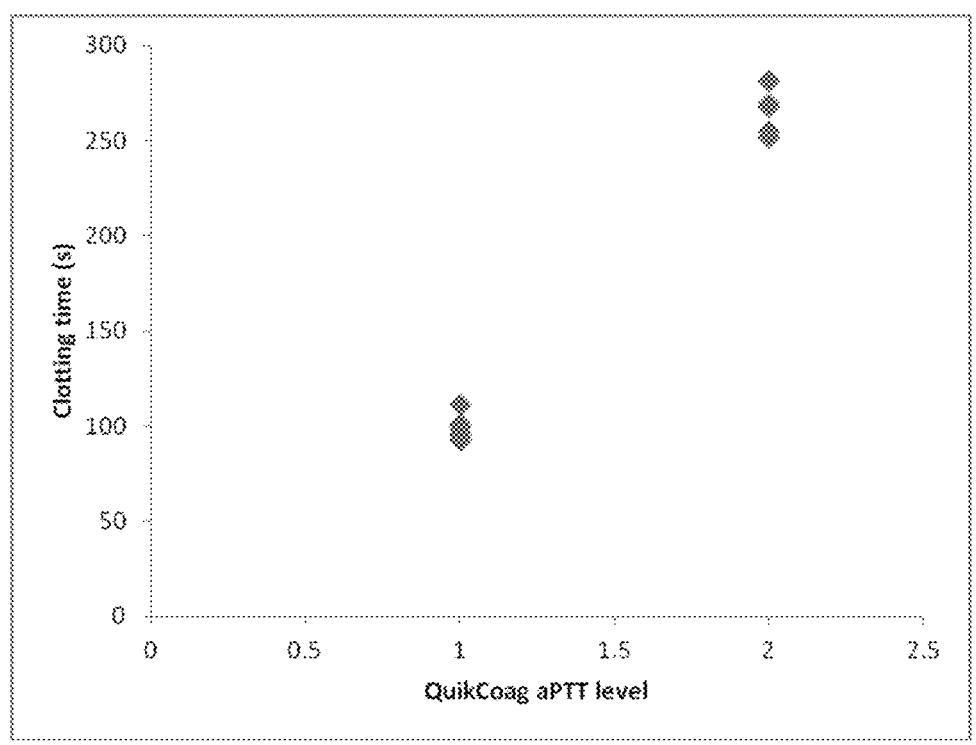
FIG. 13 shows exemplary results of measuring aPTT by bead settling.

Measurement of the aPTT coagulation parameter by bead settling was performed with the following materials:
  Plasma samples: QuikCoag™ Control Level 1 (Normal Coagulation Plasma Control) and QuikCoag™ Control Level 2 (Low Abnormal Coagulation Plasma Control) (each from BioMedica Diagnostics Inc., Nova Scotia, Canada)
  Reconstituted aPTT reagent (QuikCoag™ APTT, BioMedica Diagnostics Inc., Nova Scotia, Canada)
  Bead slurry (e.g. 1:1 mixture of 25 um and 45 um diameter beads (e.g. Polybead Microspheres, Polysciences, PA), washed in HBS, centrifuged, and excess liquid removed)
  1× HBS (Hepes Buffered Saline pH7.4)
  0.02 M $CaCl_2$ These materials were used in the following procedure to measure the aPTT coagulation parameter by bead settling. All steps were performed at room temperature, using an automated liquid handler.
1) Each plasma sample was diluted 5-fold with HBS
2) Mixed beads 1:1 with 0.2M $CaCl_2$ (e.g. 10 µl beads+10 µl 0.2M $CaCl_2$)
3) Mix 1 µl of diluted plasma with 1 µl of aPTT reagent and incubate for 3 minutes
4) At t=0, mixed 1 µl of the mixture with 1 µl of bead/$CaCl_2$ mix, and aspirated into tip.
5) Aspirated 1 µl mineral oil, dipping tip deep enough in oil to cover viewing area
6) Moved to camera and begin video recording
7) Stopped recording after clotting occurred (typically <10 minutes)
8) Repeated steps 3-7 three more times Exemplary results are shown in FIG. 13. Here, the clotting time is shown on the vertical axis and extends from 0 to 300 seconds at the top. Levels 1 and 2 on the horizontal axis refer to QuikCoag™ Control Level 1 and 2 samples, respectively. The different points for each level show the separate result of replicate assays with each of the Level 1 and 2 plasma samples. The aPTT coagulation parameter was determined by the bead sedimentation assay, as described elsewhere herein.

Example 5 aPTT Measurement by Fluorescent Microscopy

Measurement of the aPTT coagulation parameter by fluorescent microscopy is performed with the following materials:
Plasma samples: QuikCoag™ Control Level 1 (Normal Coagulation Plasma Control); QuikCoag™ Control Level 2 (Low Abnormal Coagulation Plasma Control); and QuikCoag™ Control Level 3 (High Abnormal Coagulation Plasma Control) (each from BioMedica Diagnostics Inc., Nova Scotia, Canada)
Reconstituted aPTT reagent (e.g. QuikCoag™ APTT, BioMedica Diagnostics Inc., Nova Scotia, Canada)
1× HBS (Hepes Buffered Saline pH7.4)
0.02 M $CaCl_2$+0.3% fluorescent beads by volume (e.g. FluoSpheres carboxylate-modified microspheres, 1.0 µm, crimson fluorescent (625/645) (Life Technologies #F-8816))

These materials are used in the following procedure to measure the aPTT coagulation parameter by fluorescent microscopy. All steps are performed at room temperature, using an automated liquid handler.
Dilute plasma 5-fold (with HBS)
Add 1 µl $CaCl_2$ with fluorescent beads to slide
Focus objective to view ~20% into drop above slide surface
Mix 1 ul of diluted plasma with 1 ul of aPTT reagent and incubate for 3 minutes
At t=0, add 1 µl of this mixture to $CaCl_2$/bead mixture on slide, mix well and begin recording images
Stop recording after clotting occurs (typically <10 minutes)

Example 6

PT Measurement by Fluorescent Microscopy

Measurement of the PT coagulation parameter by fluorescent microscopy was performed with the following materials:
Plasma samples: QuikCoag™ Control Level 1 (Normal Coagulation Plasma Control); QuikCoag™ Control Level 2 (Low Abnormal Coagulation Plasma Control); and QuikCoag™ Control Level 3 (High Abnormal Coagulation Plasma Control) (each from BioMedica Diagnostics Inc., Nova Scotia, Canada)
Reconstituted PT reagent (QuikCoag™ PT plus Calcium, BioMedica Diagnostics Inc., Nova Scotia, Canada)+ 0.2% fluorescent beads by volume (e.g. FluoSpheres carboxylate-modified microspheres, 1.0 µm, crimson fluorescent (625/645) (Life Technologies #F-8816))
1× HBS (Hepes Buffered Saline pH7.4)
0.02 M $CaCl_2$+0.3% fluorescent beads by volume (e.g. FluoSpheres carboxylate-modified microspheres, 1.0 µm, crimson fluorescent (625/645) (Life Technologies #F-8816))

Figure 14:
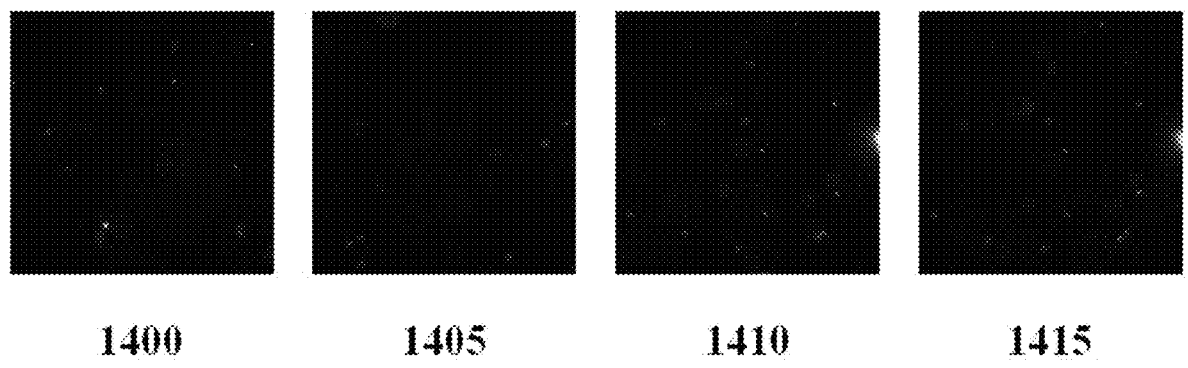
FIG. 14 shows images acquired in an exemplary fluorescent microscopy embodiment.

These materials were used in the following procedure to measure the PT coagulation parameter by fluorescent microscopy. All steps at room temperature, using an automated liquid handler.
1) Each plasma sample was diluted 5 or 10-fold with HBS
2) Added 1.5 µl PT reagent with fluorescent beads to slide
3) Focused objective to view drop ~20% into liquid column above slide surface
4) At t=0, mixed 1.5 µl of diluted plasma with bead/PT reagent mixture on slide and began recording video images
5) Stopped recording after clotting occurred (typically <10 minutes)
6) Repeated steps 4-5 two (Level 1 sample), three (Level 2 sample), or four (Level 3 sample) more times Exemplary microscopy results are shown in FIG. 14. Here, sample images were acquired after deposition of a sample with plasma (diluted 10×) and PT activation factor into a sample well. The images were taken at 5 seconds 1400, 25 seconds 1405, 50 seconds 1410, and 100 seconds 1415. The images for 50 seconds and 100 seconds were nearly identical, signifying that there was limited particle motion between 50 and 100 seconds. This implies that the motion of the particles was arrested at or before 50 seconds. Image analysis was used to determine the coagulation time using methods described above.

Figure 15:
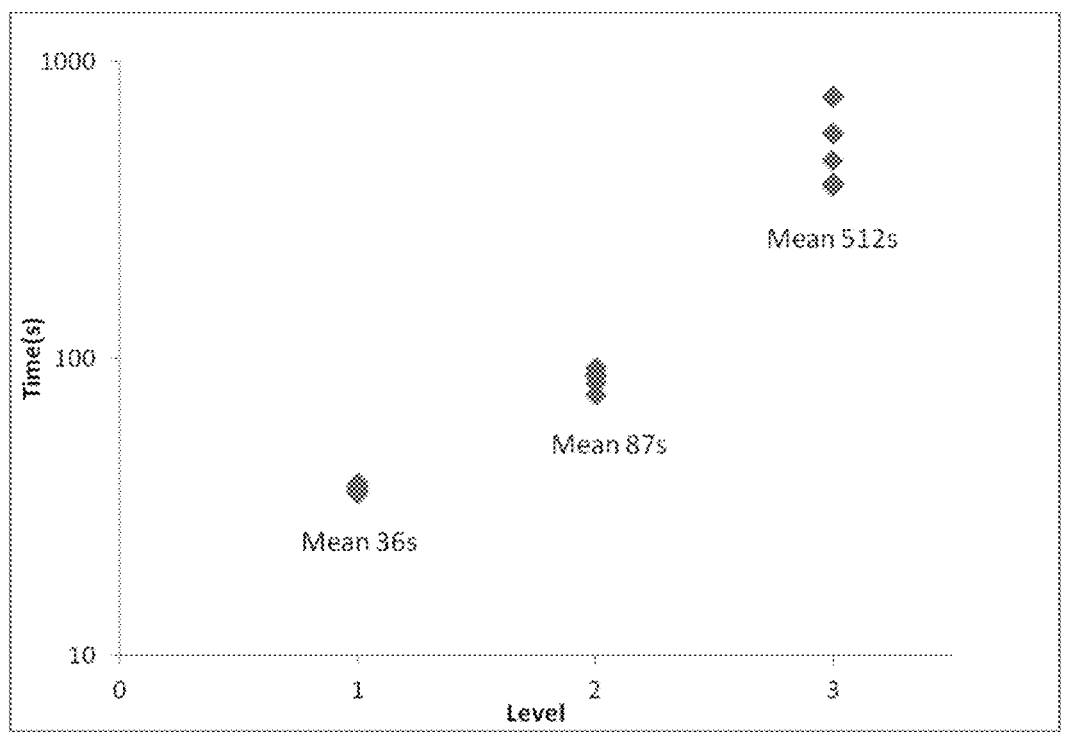
FIG. 15 shows exemplary results of measuring PT by fluorescent microscopy.

FIG. 15 shows exemplary results of PT measurement by fluorescent microscopy of 1:5 diluted plasma samples. Here, the clotting time is shown on the vertical axis on a logarithmic scale ranging from 10 to 1000 seconds. Levels 1, 2, and 3 on the horizontal axis refer to QuikCoag™ Control Level 1, 2, and 3 samples, respectively. The different points for each level show the separate result of each individual assay with each of the Level 1, 2, and 3 plasma samples. The mean value provided on the graph indicates the mean clotting time in seconds for the assays performed with each of the Level 1, 2, and 3 plasma samples.

Example 7 aPTT Measurement by Light Scattering

Measurement of the aPTT coagulation parameter by light scattering was performed with the following materials:
Human plasma containing heparin
Bovine fibrinogen (Sigma-Aldrich) 10 mg/ml stock in Hepes Buffered Saline (HBS) pH 7.4
Reconstituted aPTT reagent (QuikCoag™ APTT, BioMedica Diagnostics Inc., Nova Scotia, Canada)
1× Hepes Buffered Saline (HBS)
0.02 M $CaCl_2$ Porcine heparin (Heparin lithium salt from porcine intestinal mucosa, Sigma h0878)

These materials were used in the following procedure to measure the aPTT coagulation parameter by light scattering. All steps were performed at room temperature, using an automated liquid handler.
1) Fibrinogen was dissolved 5 mg/ml in PBS (solution A)
2) Prepared various samples of human plasma containing different concentrations of heparin. To prepare these samples, heparin was added to different human plasma aliquots to yield samples containing heparin in concentrations ranging from 0-1 U/ml.
3) Mixed 0.2 volumes of each plasma sample with 0.8 volumes solution A (i.e. each plasma sample was diluted 5-fold)
4) Mixed 5 µl of each diluted plasma with 5 µl of aPTT reagent and incubated for 3 minutes
5) At t=0, mixed 1 µl of each mixture of diluted plasma/aPTT reagent with 1 µl of 0.2M $CaCl_2$, and aspirated into a tip.
6) Aspirated 1 µl mineral oil into each tip, dipping tip deep enough in oil to cover viewing area
7) Moved to camera/photodetector and began video recording
8) Stopped recording after clotting occurred (typically <10 minutes)

Figure 16:
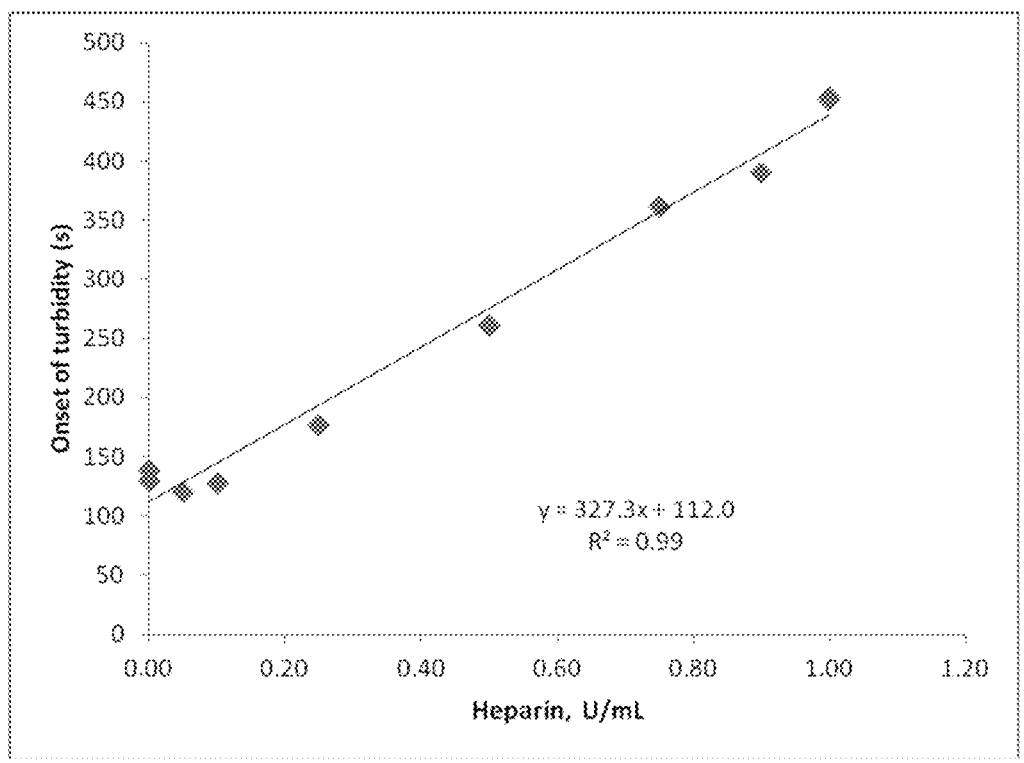
FIG. 16 shows exemplary results of the effect of added heparin to human plasma samples on coagulation time measured by light scattering

Exemplary results are shown in FIG. 16. Here, the clotting time is shown on the vertical axis in seconds. The concentration of heparin in different plasma samples in U/ml is shown on the horizontal axis. The coagulation parameter (onset of turbidity) was determined by turbidity measurements over time, as described in Example 1.

Figure 17:
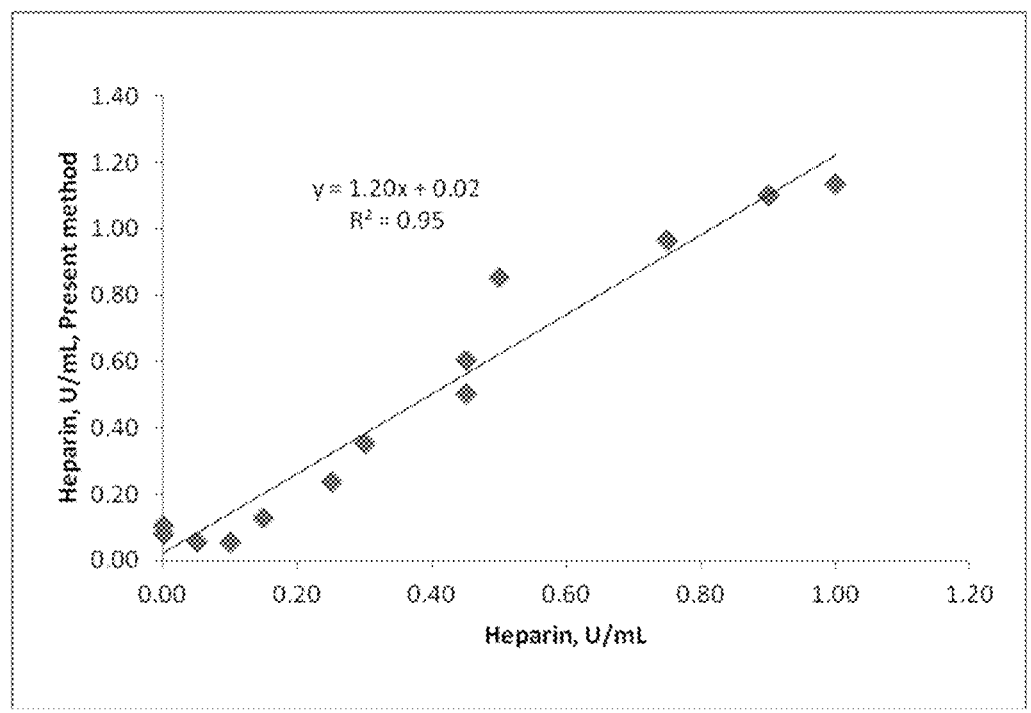
FIG. 17 shows the calibrated aPTT dose-response to heparin based on the results of FIG. 16

The dose-response of the assay of FIG. 16 was calibrated to provide an estimate of heparin concentration. The results shown in FIG. 17 confirm that the assay gave an excellent result for heparin concentration over the range of clinical interest.

In addition to performing assays as described above, aPTT assays with the plasma samples were also performed with the Helena Cascade aPTT system (Helena Laboratories, Beaumont, Tex.), according to the manufacturer's protocols. When the data from FIG. 16 were calibrated to provide an estimate of aPTT and the results compared with results using the same plasma samples on the Helena Cascade aPTT system, the following correlation was obtained: aPTT (present method)=1.00*Helena aPTT; $R^2$=0.82 indicating good agreement between the two methods.

Coagulation parameters determined by the Helena method were also correlated with the known heparin concentrations. The following was observed: y (Helena aPTT) =x (heparin concentration)*341+13.9; $R^2$=0.73 which is a poorer correlation than that of the results with the method described above (i.e. in Example 7).

Example 8

PT Measurement by Light Scattering

Measurement of the PT coagulation parameter by light scattering was performed with the following materials:
Various samples of human plasma containing EDTA, including samples from subjects on warfarin therapy and subjects not on warfarin therapy
Bovine fibrinogen (Sigma-Aldrich) 10 mg/ml stock in Hepes Buffered Saline (HBS) pH 7.4
1× Hepes Buffered Saline (HBS)

Reconstituted PT reagent (QuikCoag™ PT plus Calcium, BioMedica Diagnostics Inc., Nova Scotia, Canada) (for assay disclosed herein)
0.02 M $CaCl_2$ These materials were used in the following procedure to measure the PT coagulation parameter by light scattering. All steps were performed at room temperature, using an automated liquid handler.
1) Fibrinogen was dissolved 2.5 mg/ml in PBS (solution A)
2) Mixed 0.2 volumes of different plasma sample with 0.8 volumes solution A (i.e. each plasma sample was diluted 5-fold)
3) Prepared 5 µl aliquots of the diluted plasmas
4) At t=0, mixed this 5 µl of each diluted plasma with 5 µl of either Helena Laboratories Thromboplastin Reagent (for reference method assays) or QuikCoag™ PT plus Calcium PT reagent (for assay method disclosed herein), and aspirated 2 µl of the mixture into tip.
4) Aspirated 1 µl mineral oil, dipping tip deep enough in oil to cover viewing area
5) Moved to camera/photodetector and began recording
6) Stopped recording after clotting occurs (typically <10 minutes)

Figure 18:
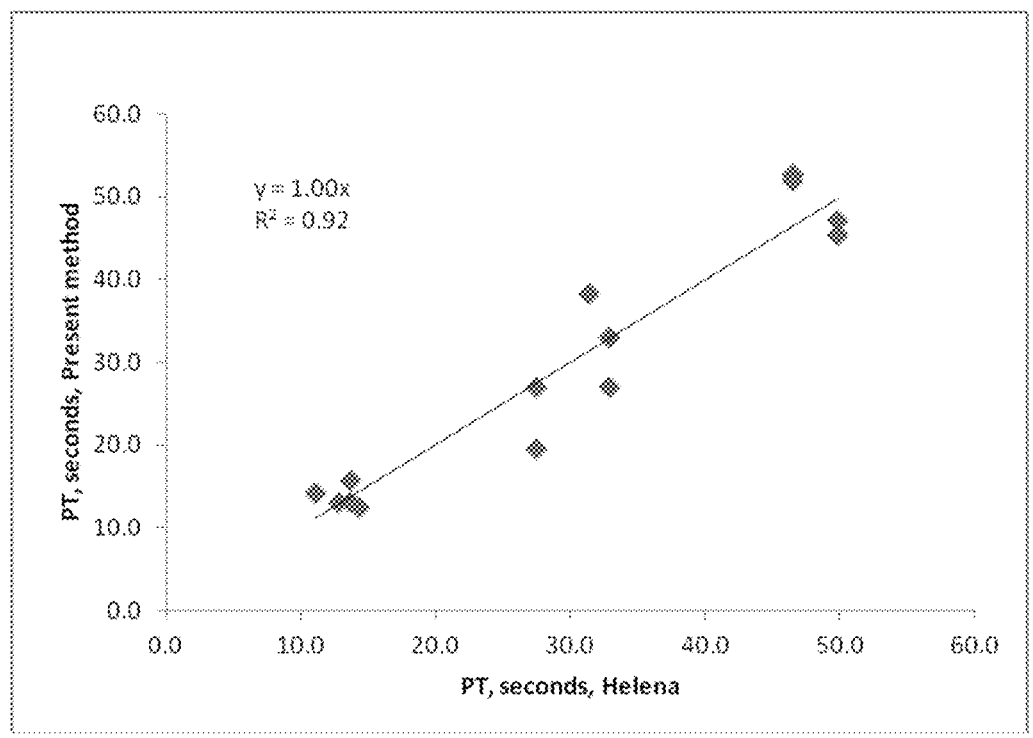
FIG. 18 shows exemplary results of measuring PT in human plasma samples (normal subjects and subjects on Warfarin therapy) by light scattering

In addition to performing assays as described above, PT assays with the plasma samples were also performed with the Helena Cascade PT system, according to the manufacturer's protocols. Exemplary results comparing the methods are shown in FIG. 18. Each point on the graph represents a different sample. Here, PT (QuikCoag™ PT plus Calcium PT reagent)=1.00(PT Helena Cascade); $R^2$=0.92.

As would be understood by a person of skill in the art, it is possible to use various alternatives, modifications and equivalents to the embodiments disclosed herein. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:
1. A device for measuring coagulation time during a coagulation reaction of a blood sample of a subject, comprising:
automated sample processing mechanisms including an automated fluid transfer apparatus;
an assay unit tip comprising a transparent wall, wherein said assay unit tip is sized to form a fluid tight seal with the automated fluid transfer apparatus and is in a vertical orientation when engaged to be moved by the automated fluid transfer apparatus while said tip holds a blood sample for coagulation measurement, a programmable processor programmed to control the automated fluid transfer apparatus;

a coagulation initiation reagent and particles to be added to the blood sample from the subject; and a detector comprising a camera configured to provide images for the detection of settling of beads or other particles in the blood sample within said assay unit tip during said coagulation reaction;

wherein said automated fluid transfer apparatus is controlled by the programmable processor to:

dilute the sample used in the coagulation reaction;

add the coagulation initiation reagent to the diluted sample under a condition suitable for clot formation, thereby initiating the coagulation reaction within said assay unit tip;

dip the assay unit tip into oil to aspirate oil and coat a viewing area of the assay unit tip with oil;

move said assay unit tip within said device near to said camera, wherein the viewing area of the assay unit tip is oil-coated when said assay unit tip is moved to said camera for inspection.

2. The device of claim 1, wherein said camera comprises a video camera configured to obtain a set of more than one image of settling of beads or other particles in the blood sample within said assay unit tip during said coagulation reaction.

3. The device of claim 2 further comprising a programmable computer that analyzes said set of images to measure the coagulation time of said blood sample.

4. The device of claim 3, wherein said computer is configured to analyze video images of settling of beads or other particles in the blood sample to determine coagulation time.

5. The device of claim 3, wherein said computer is configured to identify regions of interest (ROI) in video images of settling of beads or other particles in the blood sample, for use of a video image portion within said ROI in determining coagulation time.

6. The device of claim 2, wherein said video camera is configured to provide video images for the detection of settling of beads or other particles in the blood sample.

7. The device of claim 6, wherein said video camera is configured to provide video images for the detection of settling of beads or other particles in the blood sample, wherein said beads or other particles are labeled beads or labeled particles.

8. The device of claim 2, wherein said video camera is coupled to a microscope.

9. The device of claim 1, wherein at least a portion of the device is located at a point of service location.

10. The device of claim 1, wherein the device may be dynamically controlled through a cloud computing infrastructure.

11. The device of claim 1, wherein the entire device is located at a point of service location.

12. The device of claim 1, further comprising a computer configured to analyze images of settling of beads or other particles in the blood sample to determine coagulation time.

13. The device of claim 12, wherein said computer is configured to identify a region of interest (ROI) in images of settling of beads or other particles in the blood sample, for use of an image portion within said ROI in determining coagulation time.

14. The device of claim 1, wherein said camera is configured to provide images for the detection of settling of beads or other particles in the blood sample, wherein said beads or other particles are labeled beads or labeled particles.

15. The device of claim 1, wherein said computer is configured to analyze images of beads or other particles in the blood sample for the determination of difference parameters for said images.

16. The device of claim 1, wherein said computer is configured to analyze images of beads or other particles in the blood sample for the determination of signal-to-noise ratios for said images.

17. The device of claim 1, wherein said computer is configured to analyze images of beads or other particles in the blood sample for the determination of correlation factors for said images.

18. The device of claim 1, wherein said camera is coupled to a microscope.

19. A device for measuring coagulation time during a coagulation reaction of a blood sample of a subject, comprising:

automated sample processing mechanisms including an automated fluid transfer apparatus;

an assay unit tip comprising a transparent wall, wherein said assay unit tip is sized to form a fluid tight seal with the automated fluid transfer apparatus and is in a vertical orientation when engaged to be moved by the automated fluid transfer apparatus while said tip holds a blood sample for coagulation measurement, a programmable processor programmed to control the automated fluid transfer apparatus;

a coagulation initiation reagent and particles to be added to the blood sample from the subject; and a detector comprising a camera configured to provide images for the detection of settling of particles in the blood sample within said assay unit tip during said coagulation reaction;

wherein said automated fluid transfer apparatus is controlled by the programmable processor to:

dilute the sample used in the coagulation reaction;

add the coagulation initiation reagent to the diluted sample under a condition suitable for clot formation, thereby initiating the coagulation reaction within said assay unit tip;

dip the assay unit tip into oil to aspirate oil and coat a viewing area of the assay unit tip with oil;

move said assay unit tip within said device near to said camera, wherein the viewing area of the assay unit tip is oil-coated when said assay unit tip is moved to said camera for inspection;

wherein said particles are labeled with a fluorescent label.

20. A device for measuring coagulation time during a coagulation reaction of a blood sample of a subject, comprising:

automated sample processing mechanisms including an automated fluid transfer apparatus;

an assay unit tip comprising a transparent wall, wherein said assay unit tip is sized to form a fluid tight seal with the automated fluid transfer apparatus and is in a vertical orientation when engaged to be moved by the automated fluid transfer apparatus while said tip holds a blood sample for coagulation measurement, a programmable processor programmed to control the automated fluid transfer apparatus;

a coagulation initiation reagent and particles to be added to the blood sample from the subject; and a detector comprising a camera configured to provide images for the detection of settling of particles in the blood sample within said assay unit tip during said coagulation reaction;

wherein said automated fluid transfer apparatus is controlled by the programmable processor to:
  dilute the sample used in the coagulation reaction;
  add the coagulation initiation reagent to the diluted sample under a condition suitable for clot formation, thereby initiating the coagulation reaction within said assay unit tip;
  dip the assay unit tip into oil to aspirate oil and coat a viewing area of the assay unit tip with oil;
  move said assay unit tip within said device near to said camera, wherein the viewing area of the assay unit tip is oil-coated when said assay unit tip is moved to said camera for inspection;

wherein said particles comprise beads labeled with a fluorescent label.

* * * * *